United States Patent
Embrey et al.

(10) Patent No.: US 6,172,076 B1
(45) Date of Patent: Jan. 9, 2001

(54) INHIBITORS OF PRENYL-PROTEIN TRANSFERASE

(75) Inventors: Mark W. Embrey, North Wales; John S. Wai, Harleysville; Debra S. Perlow, East Greenville; Jacob M. Hoffman, Lansdale, all of PA (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/332,769

(22) Filed: Jun. 14, 1999

Related U.S. Application Data

(60) Provisional application No. 60/089,311, filed on Jun. 15, 1998.

(51) Int. Cl.$^7$ .................. A61K 31/438; C07D 487/10
(52) U.S. Cl. .................. 514/278; 514/303; 546/20
(58) Field of Search .................. 514/278, 303; 546/20

(56) References Cited

U.S. PATENT DOCUMENTS

| | | | |
|---|---|---|---|
| 4,244,961 | 1/1981 | Kluge et al. | 424/267 |
| 4,255,432 | 3/1981 | Kluge et al. | 424/267 |
| 5,576,313 | 11/1996 | Fisher et al. | 514/211 |
| 5,739,336 | 4/1998 | Weinhardt et al. | 546/20 |
| 5,817,678 | 10/1998 | Kim et al. | |
| 5,891,889 * | 4/1999 | Anthony et al. | 514/326 |

FOREIGN PATENT DOCUMENTS

| | | |
|---|---|---|
| 49-133380 | 12/1974 | (JP) . |
| WO95/22544 | 8/1995 | (WO) . |
| WO 97/00872 | 1/1997 | (WO) . |
| WO 97/11940 | 4/1997 | (WO) . |
| WO97/14686 | 4/1997 | (WO) . |

OTHER PUBLICATIONS

Andrew Thurkauf et al, Journal of Medicinal Chem. vol. 38, 1995.

J. Med. Chem., vol. 38, pp. 2251–2255 (1995), by Thurkauf, et al.

Exp. Opin. Ther. Patents vol. 5, No. 12, pp. 1269–1285 (1995), by S. L. Graham

Chimie Therapeutique, Mai–Juin 1969, No. 3, pp. 185–194, by G. Regnier, et al. with English translation.

Boll. Chim., Farm., vol. 121 (1982), pp. 16–26, by A. Catto, et al. with English translation.

II Farmaco, Ed. Sc., vol. 25, No. 9, pp. 681–693 (1970), by G. Winters, et al. with English translation.

J. Org. Chem. vol. 61 (1996) pp. 7650–7651, C. L. Wysong et al, "4–Aminopiperidine–4–carboxylic Acid: A Cyclic α,α–Disubstituted Amino Acid for Preparation of Water–Soluble Highly Helical Peptides".

Pharmeceutica Acta Helvetiae 69 (1994) pp. 29–37, J.–C. Dore et al, "Study of structure/activity relationships by multivariate statistical analysis in a series of triazaspirodecanediones with CNS activities".

Bioorganic & Medicinal Chemistry Letters, vol. 6, No. 22 (1996) pp. 2687–2692, K. K. Weinhardt et al, "Some Benzenesulfonamido–Substituted Valerophenones That Are Selective Antagonists for the $5-HT_{2c}$ Receptor".

Acta Chem. Scand. 22 (1968) No. 4, pp. 1353–1355, U. Michael et al, "A Simple One–pot Procedure for the Synthesis of Certain Substituted Thiophene Aldehydes and Ketones".

J. Med. Chem. vol. 24, No. 11 (1981) pp. 1320–1328, J. M. Caroon et al, "Synthesis and Antihypertensive Activity of a Series of 8–Substituted 1–Oxa–3,8–diazaspiro[4.5]decan–2–ones".

J. Med. Chem. vol. 41, No. 25 (1998) pp. 5084–5093, K. A. Metwally et al., "Spiperone: Influence of Spiro Ring Sustituents on $5-HT_{2A}$ Serotonin Receptor Binder".

Adv. Behav. Biol. vol. 29 (1986) pp. 585–592, G. Bollinger et al, "Structure–Activity Relationships of RS 86 Analogues".

* cited by examiner

*Primary Examiner*—Alan L. Rotman
*Assistant Examiner*—Rita Desai
(74) *Attorney, Agent, or Firm*—Dianne Pecoraro; Mark R. Daniel

(57) ABSTRACT

The present invention is directed to conformationally constrained compounds which inhibit prenyl-protein transferase and the prenylation of the oncogene protein Ras. The invention is further directed to chemotherapeutic compositions containing the compounds of this invention and methods for inhibiting prenyl-protein transferase and the prenylation of the oncogene protein Ras.

19 Claims, No Drawings

SEQUENCE LISTING

<160> NUMBER OF SEQ ID NOS: 21

<210> SEQ ID NO 1
<211> LENGTH: 4
<212> TYPE: PRT
<213> ORGANISM: Homosapien

<400> SEQUENCE: 1

Cys Val Leu Leu
 1

<210> SEQ ID NO 2
<211> LENGTH: 15
<212> TYPE: PRT
<213> ORGANISM: Homosapien

<400> SEQUENCE: 2

Gly Lys Lys Lys Lys Lys Ser Lys Thr Lys Cys Val Ile Met
 1               5                  10                  15

<210> SEQ ID NO 3
<211> LENGTH: 52
<212> TYPE: DNA
<213> ORGANISM: Artificial Sequence
<220> FEATURE:
<223> OTHER INFORMATION: completely synthesized

<400> SEQUENCE: 3
gagagggaat tcgggccctt cctgcatgct gctgctgctg ctgctgctgg gc            52

<210> SEQ ID NO 4
<211> LENGTH: 41
<212> TYPE: DNA
<213> ORGANISM: Artificial Sequence
<220> FEATURE:
<223> OTHER INFORMATION: completely synthesized

<400> SEQUENCE: 4
gagagagctc gaggttaacc cgggtgcgcg gcgtcggtgg t                       41

<210> SEQ ID NO 5
<211> LENGTH: 42
<212> TYPE: DNA
<213> ORGANISM: Artificial Sequence
<220> FEATURE:
<223> OTHER INFORMATION: completely synthesized

<400> SEQUENCE: 5
gagagagtct agagttaacc cgtggtcccc gcgttgcttc ct                      42

<210> SEQ ID NO 6
<211> LENGTH: 43
<212> TYPE: DNA
<213> ORGANISM: Artificial Sequence
<220> FEATURE:
<223> OTHER INFORMATION: completely synthesized

<400> SEQUENCE: 6
gaagaggaag cttggtaccg ccactgggct gtaggtggtg gct                     43

<210> SEQ ID NO 7
<211> LENGTH: 27
<212> TYPE: DNA
<213> ORGANISM: Artificial Sequence
<220> FEATURE:
<223> OTHER INFORMATION: completely synthesized

<400> SEQUENCE: 7
ggcagagctc gtttagtgaa ccgtcag                                               27

<210> SEQ ID NO 8
<211> LENGTH: 27
<212> TYPE: DNA
<213> ORGANISM: Artificial Sequence
<220> FEATURE:
<223> OTHER INFORMATION: completely synthesized

<400> SEQUENCE: 8
gagagatctc aaggacggtg actgcag                                               27

<210> SEQ ID NO 9
<211> LENGTH: 86
<212> TYPE: DNA
<213> ORGANISM: Artificial Sequence
<220> FEATURE:
<223> OTHER INFORMATION: completely synthesized

<400> SEQUENCE: 9
tctcctcgag gccaccatgg ggagtagcaa gagcaagcct aaggacccca gccagcgccg           60
gatgacagaa tacaagcttg tggtgg                                               86

<210> SEQ ID NO 10
<211> LENGTH: 33
<212> TYPE: DNA
<213> ORGANISM: Artificial Sequence
<220> FEATURE:
<223> OTHER INFORMATION: completely synthesized

<400> SEQUENCE: 10
cacatctaga tcaggacagc acagacttgc agc                                       33

<210> SEQ ID NO 11
<211> LENGTH: 41
<212> TYPE: DNA
<213> ORGANISM: Artificial Sequence
<220> FEATURE:
<223> OTHER INFORMATION: completely synthesized

<400> SEQUENCE: 11
tctcctcgag gccaccatga cagaatacaa gcttgtggtg g                              41

<210> SEQ ID NO 12
<211> LENGTH: 38
<212> TYPE: DNA
<213> ORGANISM: Artificial Sequence
<220> FEATURE:
<223> OTHER INFORMATION: completely synthesized

<400> SEQUENCE: 12
cactctagac tggtgtcaga gcagcacaca cttgcagc                                  38

<210> SEQ ID NO 13
<211> LENGTH: 38
<212> TYPE: DNA
<213> ORGANISM: Artificial Sequence
<220> FEATURE:
<223> OTHER INFORMATION: completely synthesized

<400> SEQUENCE: 13

-continued gagagaattc gccaccatga cggaatataa gctggtgg          38

<210> SEQ ID NO 14
<211> LENGTH: 33
<212> TYPE: DNA
<213> ORGANISM: Artificial Sequence
<220> FEATURE:
<223> OTHER INFORMATION: completely synthesized

<400> SEQUENCE: 14
gagagtcgac gcgtcaggag agcacacact tgc          33

<210> SEQ ID NO 15
<211> LENGTH: 22
<212> TYPE: DNA
<213> ORGANISM: Artificial Sequence
<220> FEATURE:
<223> OTHER INFORMATION: completely synthesized

<400> SEQUENCE: 15
ccgccggcct ggaggagtac ag          22

<210> SEQ ID NO 16
<211> LENGTH: 38
<212> TYPE: DNA
<213> ORGANISM: Artificial Sequence
<220> FEATURE:
<223> OTHER INFORMATION: completely synthesized

<400> SEQUENCE: 16
gagagaattc gccaccatga ctgagtacaa actggtgg          38

<210> SEQ ID NO 17
<211> LENGTH: 32
<212> TYPE: DNA
<213> ORGANISM: Artificial Sequence
<220> FEATURE:
<223> OTHER INFORMATION: completely synthesized

<400> SEQUENCE: 17
gagagtcgac ttgttacatc accacacatg gc          32

<210> SEQ ID NO 18
<211> LENGTH: 21
<212> TYPE: DNA
<213> ORGANISM: Artificial Sequence
<220> FEATURE:
<223> OTHER INFORMATION: completely synthesized

<400> SEQUENCE: 18
gttggagcag ttggtgttgg g          21

<210> SEQ ID NO 19
<211> LENGTH: 38
<212> TYPE: DNA
<213> ORGANISM: Artificial Sequence
<220> FEATURE:
<223> OTHER INFORMATION: completely synthesized

<400> SEQUENCE: 19
gagaggtacc gccaccatga ctgaatataa acttgtgg          38

<210> SEQ ID NO 20
<211> LENGTH: 36
<212> TYPE: DNA
<213> ORGANISM: Artificial Sequence

```
<220> FEATURE:
<223> OTHER INFORMATION: completely synthesized

<400> SEQUENCE: 20
ctctgtcgac gtatttacat aattacacac tttgtc                36

<210> SEQ ID NO 21
<211> LENGTH: 24
<212> TYPE: DNA
<213> ORGANISM: Artificial Sequence
<220> FEATURE:
<223> OTHER INFORMATION: completely synthesized

<400> SEQUENCE: 21
gtagttggag ctgttggcgt aggc                             24
```

INHIBITORS OF PRENYL-PROTEIN TRANSFERASE

DOMESTIC PRIORITY CLAIM

This application claims priority form the U.S. Provisional Application No. 60/089,311, filed on Jun. 15, 1998.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1). Compounds containing piperazines, piperazinones, piperidines and piperidinones have also been observed to be inhibitors of FPTase (WO 97/37900, WO 97/36605, and WO 97/38665).

It is, therefore, an object of this invention to develop compounds that do not have a thiol moiety, and that will inhibit prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises conformationally constrained compounds that do not resemble peptides and which inhibit prenyl-protein transferase. Further contained in this invention are chemotherapeutic compositions containing these prenyl-protein transferase inhibitors and methods for their production.

The compounds of this invention are illustrated by the formula I:

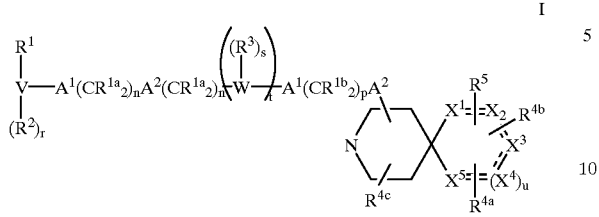

DETAILED DESCRIPTION OF THE INVENTION

The compounds of this invention are useful in the inhibition of prenyl-protein transferase and the prenylation of the oncogene protein Ras. In an embodiment of this invention, the inhibitors of prenyl-protein transferase are illustrated by the formula I:

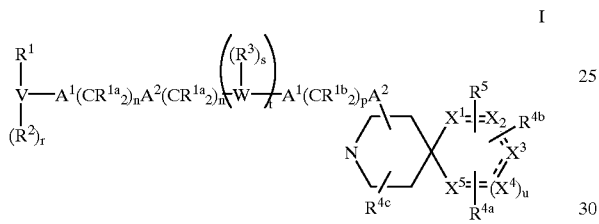

wherein:
$R^{1a}$ and $R^{1b}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, $CN$, $NO_2$, $(R^8)_2N$—$C(NR^8)$—, $R^8C(O)$—, $R^8OC(O)$—, $N_3$, —$N(R^8)_2$, or $R^9OC(O)NR^8$—,
  c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, $CN$, $(R^8)_2N$—$C(NR^8)$—, $R^8C(O)$—, $R^8OC(O)$—, $N_3$, —$N(R^8)_2$, or $R^9OC(O)$—$NR^8$—;

$R^1$ and $R^2$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, $CN$, $NO_2$, $R^8{}_2N$—$C(NR^8)$—, $R^8C(O)$—, $R^8OC(O)$—, $N_3$, —$N(R^8)_2$, or $R^9OC(O)NR^8$—, and
  c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, $CN$, $H_2N$—$C(NH)$—, $R^8C(O)$—, $R^8OC(O)$—, $N_3$, —$N(R^8)_2$, or $R^8OC(O)NH$—;

$R^3$ is selected from:
  a) hydrogen,
  b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, $CN$, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
  c) $C_1$–$C_6$ alkyl, unsubstituted or substituted by perfluoroalkyl, F, Cl, Br, $R^8O$—, $R^9S(O)_m$—, $R^8C(O)NR^8$—, $CN$, $(R^8)_2N$—$C(NR^8)$—, $R^8C(O)$—, $R^8OC(O)$—, $N_3$, —$N(R^8)_2$, or $R^9OC(O)NR^8$—;

$R^{4a}$, $R^{4b}$, $R^{4c}$ and $R^5$ independently are selected from:
  H, =O, unsubstituted or substituted $C_{1-8}$ alkyl, unsubstituted or substituted $C_{2-8}$ alkenyl, unsubstituted or substituted aryl, unsubstituted or substituted heterocycle,

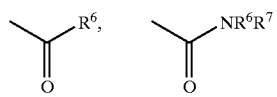

and —$S(O)_2R^6$, wherein the substituted group is substituted with one or more of:
  1) aryl or heterocycle, unsubstituted or substituted with one or two groups selected from:
     a) $C_{1-4}$ alkyl,
     b) $(CH2)_pOR^6$,
     c) $(CH2)_pNR^6R^7$,
     d) halogen,
     e) $C_{1-4}$ perfluoroalkyl,
  2) $C_{3-6}$ cycloalkyl,
  3) $OR^6$,
  4) $SR^6$, $S(O)R^6$, $SO^2R^6$,
  5) —$NR^6R^7$ 6)
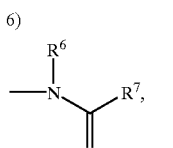

7)
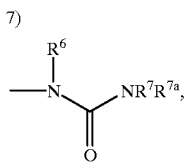

8)
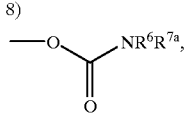

9)
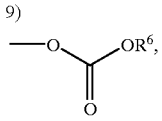

10)
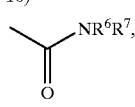

11)
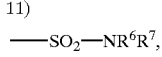

12)
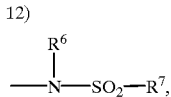

-continued

13)

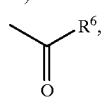

14)

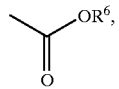

15) $C_{1-8}$ alkyl,
16) $C_{1-8}$ perfluoroalkyl, or
17) halo;

either $R^{4b}$ and $R^5$ or $R^{4a}$ and $R^{4b}$, when located on adjacent carbon atoms, may be joined to form a ring;

$R^6$, $R^7$ and $R^{7a}$ are independently selected from: H, $C_{1-4}$ alkyl, $C_{3-6}$ cycloalkyl, heterocycle, aryl, $C_{1-4}$ perfluoroalkyl, unsubstituted or substituted with one or two substituents selected from:
  a) $C_{1-4}$ alkoxy,
  b) substituted or unsubstituted aryl or substituted or unsubstituted heterocycle,
  c) halogen,
  d) HO,
  e)

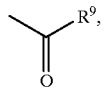

f)

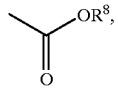

g) —S(O)$_m$R$^9$, or
  h) N(R$^8$)$_2$; or $R^6$ and $R^7$ may be joined in a ring;
$R^7$ and $R^{7a}$ may be joined in a ring;
$R^8$ is independently selected from hydrogen, $C_1$–$C_6$ alkyl, benzyl, 2,2,2-trifluoroethyl and aryl;
$R^9$ is independently selected from $C_1$–$C_6$ alkyl and aryl;
$A^1$ and $A^2$ are independently selected from:
  a) a bond,
  b) HC=CH,
  c) C≡C,
  d) O,
  e) C=O,
  f) O=C,
  g) —C(O)NR$^8$—,
  h) —NR$^8$C(O)—,
  i) —N(R$^8$)—,
  j) —S(O)$_2$N(R$^8$)—,
  k) —N(R$^8$)S(O)$_2$—, or
  l) S(O)$_m$;

$X^1$, $X^2$, $X^3$, $X^4$ and $X^5$ are independently selected from: C(H)$_y$, N(H)$_w$, O, C=O, S(O)$_2$, and PO(OMe);

V is selected from:
  a) hydrogen,
  b) heterocycle,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;
  provided that if V is hydrogen then R$^1$ is absent;

W is heterocycle;
m is 0,1 or 2;
n is 0, 1, 2, 3 or 4;
p is 0, 1, 2, 3 or 4;
r is independently 0 to 5, provided that r is 0 when V is hydrogen;
s is 1 or 2;
t is 0 or 1;
u is 0, 1 or 2;
w is 0 or 1; and
is 1 or 2;

dashed lines represent optional double bonds or the pharmaceutically acceptable salts or the optical isomers thereof.

In a further embodiment of this invention, the inhibitors of prenyl-protein transferase are illustrated by the formula I:

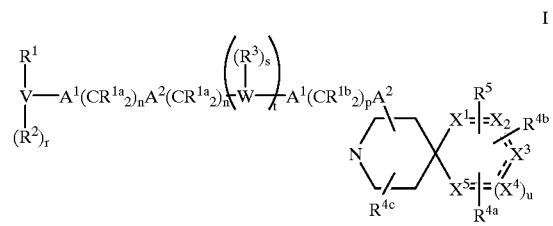

wherein $R^{1a}$ and $R^{1b}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—,
  c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)—NR$^8$—;

$R^1$ and $R^2$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, R$^8$O—, R$^9$S(O)$_m$—, R$^8$C(O)NR$^8$—, CN, NO$_2$, R$^8$$_2$N—C(NR$^8$)—, R$^8$C(O)—, R$^8$OC(O)—, N$_3$, —N(R$^8$)$_2$, or R$^9$OC(O)NR$^8$—, and
  c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, R$^8$O—, R$^9$S(O)$_m$—, R$^8$C(O)NH—, CN, H$_2$N—C(NH)—, R$^8$C(O)—, R$^8$OC(O)—, N$_3$, —N(R$^8$)$_2$, or R$^8$OC(O)NH—;

$R^3$ is selected from:
  a) hydrogen,
  b) $C_2$–$C_6$ alkenyl, $C_2$–$C_6$ alkynyl, $C_3$–$C_6$ cycloalkyl, perfluoroalkyl, F, Cl, Br, R$^8$O—, R$^9$S(O)$_m$—, R$^8$C(O)NR$^8$—, CN, NO$_2$, (R$^8$)$_2$N—C—(NR$^8$)—, R$^8$C(O)—, R$^8$OC(O)—, N$_3$, —N(R$^8$)$_2$, or R$^9$OC(O)NR$^8$—, and c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^{4a}$, $R^{4b}$, $R^{4c}$ and $R^5$ independently are selected from:

H, =O, unsubstituted or substituted $C_{1-8}$ alkyl, unsubstituted or substituted $C_{2-8}$ alkenyl, unsubstituted or substituted aryl, unsubstituted or substituted heterocycle,

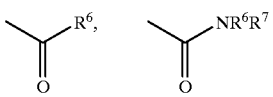

and —$S(O)_2R^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) —NR6R$^7$ 6) 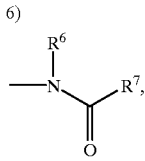

7) 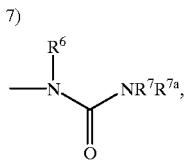

8) 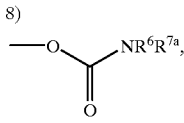

9) 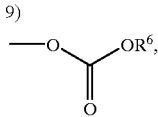

10) 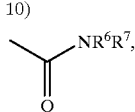

11) —$SO_2$—$NR^6R^7$,

12) 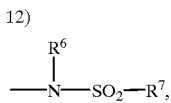

13) 

14) 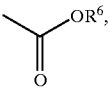

15) $C_{1-8}$ alkyl,
16) $C_{1-8}$ perfluoroalkyl, or
17) halo;

either $R^{4b}$ and $R^5$ or $R^{4a}$ and $R^{4b}$, when located on adjacent carbon atoms, may be joined to form a ring;

$R^6$, $R^7$ and $R^{7a}$ are independently selected from: H, $C_{1-4}$ alkyl, $C_{3-6}$ cycloalkyl, heterocycle, aryl, $C_{1-4}$ perfluoroalkyl, unsubstituted or substituted with one or two substituents selected from:
a) $C_{1-4}$ alkoxy,
b) substituted or unsubstituted aryl or substituted or unsubstituted heterocycle,
c) halogen,
d) HO, e) 

f) 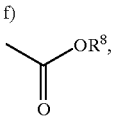

g) —$S(O)_mR^9$, or
h) $N(R^8)_2$; or $R^6$ and $R^7$ may be joined in a ring;

$R^7$ and $R^{7a}$ may be joined in a ring;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$A^1$ and $A^2$ are independently selected from:
a) a bond,
b) HC=CH,
c) C≡C
d) O,
e) C=O,
f) O=C,
g) —$C(O)NR^8$—,
h) —$NR^8C(O)$—,
i) —$N(R^8)$—,
j) —$S(O)_2N(R^8)$—,
k) —$N(R^8)S(O)_2$—, or
l) $S(O)_m$;

$X^1$, $X^2$, and $X^4$ are independently selected from: $C(H)_y$, $N(H)_w$, O, C=O, $S(O)_2$, and PO(OMe);

$X^3$ is selected from $N(H)_w$ or O;

$X^5$ is selected from C=O or $C(H)_y$;

V is selected from:
a) hydrogen,
b) heterocycle, selected from pyrrolidinyl, triazolyl, pyridyl, imidazolyl, pyridinyl, thiazolyl, indolyl, quinolinyl, or isoquinolinyl;

c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is $S(O)_m$ and V is not hydrogen if $A^1$ is a bond, n is 0 and $A^2$ is $S(O)_m$;
provided that if V is hydrogen then $R^1$ is absent;
W is a heterocycle selected from pyrrolidinyl, triazolyl, imidazolyl, pyridyl, pyridinyl, thiazolyl, indolyl, quinolinyl, or isoquinolinyl;
m is 0, 1 or 2;
n is 0, 1, 2, 3 and 4;
p is 0, 1, 2, 3 and 4;
r is independently 0 to 5, provided that r is 0 when V is hydrogen;
s is 1 or 2;
t is 0 or 1;
u is 0,1or 2;
w is 0 or 1; and
y is 1 or 2;
dashed lines represent optional double bonds
or the pharmaceutically acceptable salts or the optical isomers thereof.

In another embodiment of this invention, the inhibitors of prenyl-protein transferase are illustrated by the formula II:

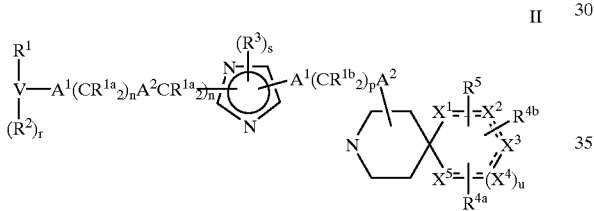

II wherein
$R^{1a}$ and $R^{1b}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;
$R^1$ and $R^2$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R_82N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^3$ is selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^{4a}$, $R^{4b}$ and $R^5$ independently are selected from:
H, =O, unsubstituted or substituted $C_{1-8}$ alkyl, unsubstituted or substituted $C_{2-8}$ alkenyl, unsubstituted or substituted aryl, unsubstituted or substituted heterocycle,

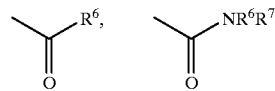

and —$S(O)_2R^6$, wherein the substituted group is substituted with one or more of:
1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) —N $R^6R^7$ 6)
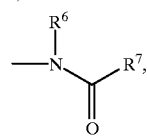

7)
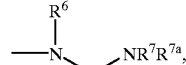

8)
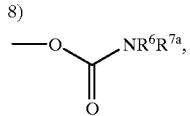

9)
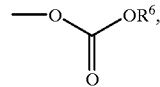

10)
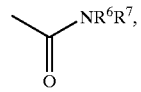

11)
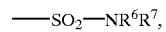

-continued

12)

$$\text{---N(R}^6\text{)---SO}_2\text{---R}^7,$$

13)

$$\text{---C(=O)---R}^6,$$

14)

$$\text{---C(=O)---OR}^6,$$

15) $C_{1-8}$ alkyl,
16) $C_{1-8}$ perfluoroalkyl, or
17) halo;

either $R^{4b}$ and $R^5$ or $R^{4a}$ and $R^{4b}$, when located on adjacent carbon atoms, may be joined to form a ring;

$R^6$, $R^7$ and $R^{7a}$ are independently selected from: H, $C_{1-4}$ alkyl, $C_{3-6}$ cycloalkyl, heterocycle, aryl, $C_{1-4}$ perfluoroalkyl, unsubstituted or substituted with one or two substituents selected from:
 a) $C_{1-4}$ alkoxy,
 b) substituted or unsubstituted aryl or substituted or unsubstituted heterocycle,
 c) halogen,
 d) HO, e)
 $$\text{---C(=O)---R}^9,$$

f)
 $$\text{---C(=O)---OR}^8,$$

g) —S(O)$_m$R$^9$, or
 h) N(R$^8$)$_2$; or $R^6$ and $R^7$ may be joined in a ring;
$R^7$ and $R^{7a}$ may be joined in a ring;
$R^8$ is independently selected from hydrogen, $C_1$–$C_6$ alkyl, benzyl, 2,2,2-trifluoroethyl and aryl;
$R^9$ is independently selected from $C_1$–$C_6$ alkyl and aryl;
$A^1$ and $A^2$ are independently selected from:
 a) a bond,
 b) HC=CH,
 c) C≡C,
 d) O,
 e) C=O,
 f) O=C,
 g) —C(O)NR$^8$—,
 h) —NR$^8$C(O)—,
 i) —N(R$^8$)—,
 j) —S(O)$_2$N(R$^8$)—,
 k) —N(R$^8$)S(O)$_2$—, or
 l) S(O)$_m$;

$X^1$, $X^2$, and $X^4$ are independently selected from:
 C(H)$_y$, N(H)$_w$, O, C=O, S(O)$_2$, and PO(OMe);

$X^3$ is selected from N(H)$_w$ or O;

$X^5$ is selected from C=O or C(H)y;

V is selected from:
 a) hydrogen,
 b) heterocycle, selected from pyrrolidinyl, triazolyl, imidazolyl, pyridinyl, thiazolyl, indolyl, quinolinyl, or isoquinolinyl;
 c) aryl,
 d) $C_1$–$C_{20}$ alkyl wherein from 0 to 4 carbon atoms are replaced with a a heteroatom selected from O, S, and N, and
 e) $C_2$–$C_{20}$ alkenyl,
 provided that V is not hydrogen if $A^1$ is S(O)$_m$ and V is not hydrogen if $A^1$ is a bond, n is 0 and $A^2$ is S(O)$_m$;
 provided that if V is hydrogen then $R^1$ is absent;

m is 0, 1 or 2;
n is 0, 1, 2, 3 and 4;
p is 0, 1, 2, 3 and 4;
r is independently 0 to 5, provided that r is 0 when V is hydrogen;
s is 1 or 2;
u is 0, 1 or 2;
w is 0 or 1; and
y is 1 or 2;
dashed lines represent optional double bonds
or the pharmaceutically acceptable salts or the optical isomers thereof.

In another embodiment of this invention, the inhibitors of prenyl-protein transferase are illustrated by the formula III:

III $$R^1\text{---}\bigcirc\text{---}A^1(CR^{1a}_2)_nA^2CR^{1a}_2\text{---}\bigcirc\text{(R}^3)_s\text{---}A^1(CR^{1b}_2)_pA^2\text{---}\bigcirc\text{---}...$$
(R$^2$)$_r$ wherein:

$R^{1a}$ and $R^{1b}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—;
 c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, R$^8$O—, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)-NR^8-$;

$R^1$ and $R^2$ are independently selected from:
a) hydrogen,
b) unsubstituted or substituted aryl, unsubstituted or substituted heterocycle, $C_3-C_{10}$ cycloalkyl, $C_2-C_6$ alkenyl, $C_2-C_6$ alkynyl, perfluoroalkyl, F, Cl, Br, $R^8O-$, $R^9S(O)_m-$, $R^8C(O)NR^8-$, CN, $NO_2$, $R^8{}_2N-C(NR^8)-$, $R^8C(O)-$, $R^8OC(O)-$, $N_3$, $-N(R^8)_2$, or $R^9OC(O)NR^8-$, and
c) $C_1-C_6$ alkyl unsubstituted or substituted by aryl, heterocycle, $C_3-C_{10}$ cycloalkyl, $C_2-C_6$ alkenyl, $C_2-C_6$ alkynyl, perfluoroalkyl, F, Cl, Br, $R^8O-$, $R^9S(O)_m-$, $R^8C(O)NH-$, CN, $H_2N-C(NH)-$, $R^8C(O)-$, $R^8OC(O)-$, $N_3$, $-N(R^8)_2$, or $R^8OC(O)NH-$;

$R^3$ is selected from:
a) hydrogen,
b) $C_2-C_6$ alkenyl, $C_2-C_6$ alkynyl, $C_3-C_6$ cycloalkyl, perfluoroalkyl, F, Cl, Br, $R^8O-$, $R^9S(O)_m-$, $R^8C(O)NR^8-$, CN, $NO_2$, $(R^8)_2N-C-(NR^8)-$, $R^8C(O)-$, $R^8OC(O)-$, $N_3$, $-N(R^8)_2$, or $R^9OC(O)NR^8-$, and
c) $C_1-C_6$ alkyl, unsubstituted or substituted by perfluoroalkyl, F, Cl, Br, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$;

$R^{4a}$, $R^{4b}$ and $R^5$ independently are selected from:
H, =O, unsubstituted or substituted $C_{1-8}$ alkyl, unsubstituted or substituted $C_{2-8}$ alkenyl, unsubstituted or substituted aryl, unsubstituted or substituted heterocycle,

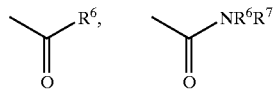

and $-S(O)_2R^6$, wherein the substituted group is substituted with one or more of:
1) aryl or heterocycle, unsubstituted or substituted with one or two groups selected from:
  a) $C_{1-4}$ alkyl,
  b) $(CH_2)_pOR^6$,
  c) $(CH_2)_pNR^6R^7$,
  d) halogen,
  e) $C_{1-4}$ perfluoroalkyl,
2) $C_{3-6}$ cycloalkyl,
3) $OR^6$,
4) $SR^6$, $S(O)R^6$, $SO_2R^6$,
5) $-NR^6R^7$ 6)
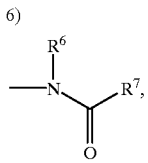

7)
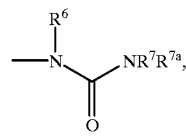

8)
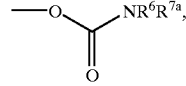

9)
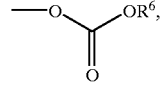

10)
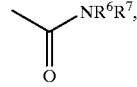

11) $-SO_2-NR^6R^7$,

12)
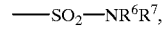

13)
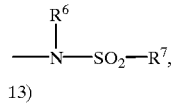

14)
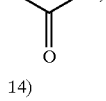

15) $C_{1-8}$ alkyl,
16) $C_{1-8}$ perfluoroalkyl, or
17) halo;

either $R^{4b}$ and $R^5$ or $R^{4a}$ and $R^{4b}$, when located on adjacent carbon atoms, may be joined to form a ring;

$R^6$, $R^7$ and $R^{7a}$ are independently selected from: H, $C_{1-4}$ alkyl, $C_{3-6}$ cycloalkyl, heterocycle, aryl, $C_{1-4}$ perfluoroalkyl, unsubstituted or substituted with one or two substituents selected from:
a) $C_{1-4}$ alkoxy,
b) substituted or unsubstituted aryl or substituted or unsubstituted heterocycle,
c) halogen,
d) HO, e)
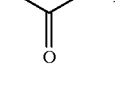

f)
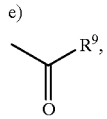

g) $-S(O)_mR^9$, or
h) $N(R^8)_2$; or $R^6$ and $R^7$ may be joined in a ring;

$R^7$ and $R^{7a}$ may be joined in a ring;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$A^1$ and $A^2$ are independently selected from:
  a) a bond,
  b) HC=CH,
  c) C≡C,
  d) O,
  e) C=O,
  f) O=C,
  g) —C(O)NR$^8$—,
  h) —NR$^8$C(O)—,
  i) —N(R$^8$)—,
  j) —S(O)$_2$N(R$^8$)—,
  k) —N(R$^8$)S(O)$_2$—, or
  l) S(O)$_m$;

$X^1$, $X^2$, and $X^4$ are independently selected from: C(H)$_y$, N(H)$_w$, O, C=O, S(O)$_2$, and PO(OMe);

$X^3$ is selected from N(H)$_w$ or O;

$X^5$ is selected from C=O or C(H)y;

m is 0, 1 or 2;

n is 0, 1, 2, 3 or 4;

p is 0, 1, 2, 3 or 4;

r is independently 0 to 5;

s is 1 or 2;

u is 0, 1 or 2;

w is 0 or 1; and y is 1 or 2;

dashed lines represent optional double bonds or the pharmaceutically acceptable salts or the optical isomers thereof.

In another embodiment of this invention, the inhibitors of prenyl-protein transferase are illustrated by formula IV:

$R^2$ is selected from:
  a) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8$O—, $R^9$S(O)$_m$—, $R^8$C(O)NR$^8$—, CN, NO$_2$, $R^8_2$N—C(NR$^8$)—, $R^8$C(O)—, $R^8$OC(O)—, N$_3$, —N(R$^8$)$_2$, or $R^9$OC(O)NR$^8$—, and
  b) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8$O—, $R^9$S(O)$_m$—, $R^8$C(O)NH—, CN, H$_2$N—C(NH)—, $R^8$C(O)—, $R^8$OC(O)—, N$_3$, —N(R$^8$)$_2$, or $R^8$OC(O)NH—;

$R^3$ is selected from:
  a) hydrogen,
  b) $C_2$–$C_6$ alkenyl, $C_2$–$C_6$ alkynyl, $C_3$–$C_6$ cycloalkyl, perfluoroalkyl, F, Cl, Br, $R^8$O—, $R^9$S(O)$_m$—, $R^8$C(O)NR$^8$—, CN, NO$_2$, $(R^8)_2$N—C—(NR$^8$)—, $R^8$C(O)—, $R^8$OC(O)—, N$_3$, —N(R$^8$)$_2$, or $R^9$OC(O)NR$^8$—, and
  c) $C_1$–$C_6$ alkyl, unsubstituted or substituted by perfluoroalkyl, F, Cl, Br, $R^8$O—, $R^9$S(O)$_m$—, $R^8$C(O)NR$^8$—, CN, $(R^8)_2$N—C(NR$^8$)—, $R^8$C(O)—, $R^8$OC(O)—, N$_3$, —N(R$^8$)$_2$, or $R^9$OC(O)NR$^8$—;

$R^{4a}$, $R^{4b}$ and $R^5$ independently are selected from:
  H, =O, unsubstituted or substituted $C_{1-8}$ alkyl, unsubstituted or substituted $C_{2-8}$ alkenyl, unsubstituted or substituted aryl, unsubstituted or substituted heterocycle, $$\overset{R^6,}{\underset{O}{\diagdown\!\!\!\diagup}} \quad \overset{NR^6R^7}{\underset{O}{\diagdown\!\!\!\diagup}}$$

and —S(O)$_2$R$^6$, wherein the substituted group is substituted with one or more of:

IV

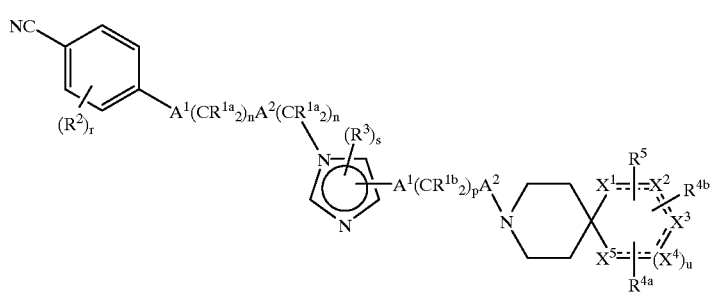

wherein $R^{1a}$ and $R^{1b}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8$O—, $R^9$S(O)$_m$—, $R^8$C(O)NR$^8$—, CN, NO$_2$, $(R^8)_2$N—C(NR$^8$)—, $R^8$C(O)—, $R^8$OC(O)—, N$_3$, —N(R$^8$)$_2$, or $R^9$OC(O)NR$^8$—,
  c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8$O—, $R^9$S(O)$_m$—, $R^8$C(O)NR$^8$—, CN, $(R^8)_2$N—C(NR$^8$)—, $R^8$C(O)—, $R^8$OC(O)—, N$_3$, —N(R$^8$)$_2$, or $R^9$OC(O)—NR$^8$—;

1) aryl or heterocycle, unsubstituted or substituted with one or two groups selected from:
  a) $C_{1-4}$ alkyl,
  b) (CH$_2$)$_p$OR$^6$,
  c) (CH$_2$)$_p$NR$^6$R$^7$,
  d) halogen,
  e) $C_{1-4}$ perfluoroalkyl,
2) $C_{3-6}$ cycloalkyl,
3) OR$^6$,
4) SR$^6$, S(O)R$^6$, SO$^2$R$^6$,

5) —NR⁶R⁷

6) 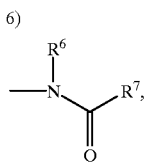

7) 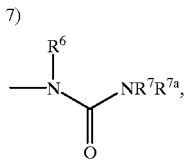

8) 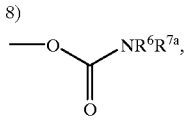

9) 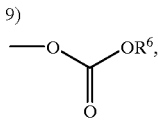

10) 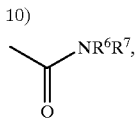

11) 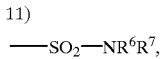

12) 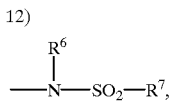

13) 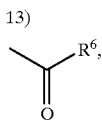

14) 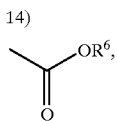

15) $C_{1-8}$ alkyl,
16) $C_{1-8}$ perfluoroalkyl, or
17) halo;

either $R^{4b}$ and $R^5$ or $R^{4a}$ and $R^{4b}$, when located on adjacent carbon atoms, may be joined to form a ring;

$R^6$, $R^7$ and $R^{7a}$ are independently selected from: H, $C_{1-4}$ alkyl, $C_{3-6}$ cycloalkyl, heterocycle, aryl, $C_{1-4}$ perfluoroalkyl, unsubstituted or substituted with one or two substituents selected from:
a) $C_{1-4}$ alkoxy,
b) substituted or unsubstituted aryl or substituted or unsubstituted heterocycle,
c) halogen,
d) HO, e) 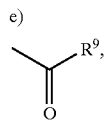

f) 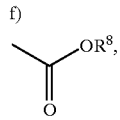

g) —S(O)ₘR⁹, or
h) N(R⁸)₂; or $R^6$ and $R^7$ may be joined in a ring;
$R^7$ and $R^{7a}$ may be joined in a ring;
$R^8$ is independently selected from hydrogen, $C_1$–$C_6$ alkyl, benzyl, 2,2,2-trifluoroethyl and aryl;
$R^9$ is independently selected from $C_1$–$C_6$ alkyl and aryl;
$A^1$ and $A^2$ are independently selected from:
a) a bond,
b) HC=CH,
c) C≡C,
d) O,
e) C=O,
f) O=C,
g) —C(O)NR⁸—,
h) —NR⁸C(O)—,
i) —N(R⁸)—,
j) —S(O)₂N(R⁸)—,
k) —N(R⁸)S(O)₂—, or
l) S(O)ₘ;

$X^1$, $X^2$, and $X^4$ are independently selected from: C(H)_y, N(H)_w, O, C=O, S(O)₂, and PO(OMe);
$X^3$ is NH or O;
$X^5$ is C=O or CH₂;
m is 0, 1 or 2;
n is 0, 1, 2, 3 or 4;
p is 0, 1, 2, 3 or 4;
r is 0, 1, 2, 3 or 4;
s is 1 or 2;
u is 0, 1 or 2;
w is 0 or 1; and
y is 1 or 2;
dashed lines represent optional double bonds or the pharmaceutically acceptable salts or the optical isomers thereof.

Specific example of the compounds of the invention are:
4-[5-(4-Oxo-1-phenyl-1,3,8-triazaspiro[4.5]dec-8-ylmethyl)imidazol-1-ylmethyl]benzonitrile;
4-{5-[4-Oxo-1-(3-methylphenyl)-1,3,8-triazaspiro[4.5]dec-8-ylmethyl]imidazol-1-ylmethyl}benzonitrile;
4-{5-[4-Oxo-1-(4-methylphenyl)-1,3,8-triazaspiro[4.5]dec-8-ylmethyl]imidazol-1-ylmethyl}benzonitrile;
4-{5-[2,4-Dioxo-1-(3-methylphenyl)-1,3,8-triaza-spiro[4.5]dec-8-ylmethyl]imidazol-1-ylmethyl}benzonitrile;
4-{5-[2-Oxo-1-(3-methylphenyl)-1,3,8-triaza-spiro[4.5]dec-8-ylmethyl]imidazol-1-ylmethyl}benzonitrile;
4-{5-[2,2-Dioxo-1-(3-methylphenyl)-2-thia-1,3,8-triazaspiro[4.5]dec-8-ylmethyl]imidazol-1-ylmethyl}benzonitrile;

4-{5-[2,2-Dioxo-1-(4-chloro-3-methylphenyl)-2-thia-1,3,8-triazaspiro[4.5]dec-8-ylmethyl]imidazol-1-ylmethyl}benzonitrile;

4-{5-[2-Oxo-1-(3-methylphenyl)-3-oxa-1,8-diazaspiro[4.5]dec-8-ylmethyl]imidazol-1-ylmethyl}benzonitrile;

4-{5-(1-Oxo-3,4-benzo-2,9-diazaspiro[5.5]undec-9-ylmethyl)imidazol 1-ylmethyl}benzonitrile;

4-[5-(3,4-Benzo-8-azaspiro[4.5]-1-decen-8-ylmethyl)-imidazol-1-ylmethyl}benzonitrile;

4-[5-(4-Oxo-3-(3-trifluoromethoxybenzyl)-1-phenyl-1,3,8-triazaspiro[4.5]dec-8-ylmethyl)imidazol-1-ylmethyl}benzonitrile;

4-[5-(4-Oxo-3-(2-trifluoromethoxybenzyl)-1-phenyl-1,3,8-triazaspiro[4.5]dec-8-ylmethyl)imidazol-1-ylmethyl}benzonitrile;

4-[5-(2-Oxo-3-(3-trifluoromethoxybenzyl)-1-oxa-3,8-diaza-spiro[4.5]dec-8-ylmethyl)imidazol-1-ylmethyl}benzonitrile;

4-[5-(2-Oxo-3-(2-trifluoromethoxybenzyl)-1-oxa-3,8-diaza-spiro[4.5]dec-8-ylmethyl)imidazol-1-ylmethyl}benzonitrile;

4-[5-(2-Oxo-3-n-butyl-1-oxa-3,8-diaza-spiro[4.5]dec-8-ylmethyl)imidazol-1-ylmethyl}benzonitrile;

4-[5-(2-Oxo-3-(2,2,2-trifluoroethyl)-1-oxa-3,8-diaza-spiro[4.5]dec-8-ylmethyl)imidazol-1-ylmethyl}benzonitrile;

4-[5-(spiro[3H-indole-3,4'-piperidin]-2(1H)-on-1'-ylmethyl)imidazol-1-ylmethyl}benzonitrile; and 4-[5-(1,3-Dioxo-2-(3-trifluoromethoxybenzyl)-2,8-diaza-spiro[4.5]dec-8-ylmethyl)imidazol-1-ylmethyl}benzonitrile or the pharmaceutically acceptable salts thereof.

Preferred examples of the compounds of the instant invention are:

4-{5-[4-Oxo-1-(3-methylphenyl)-1,3,8-triazaspiro[4.5]dec-8-ylmethyl]imidazol-1-ylmethyl}benzonitrile

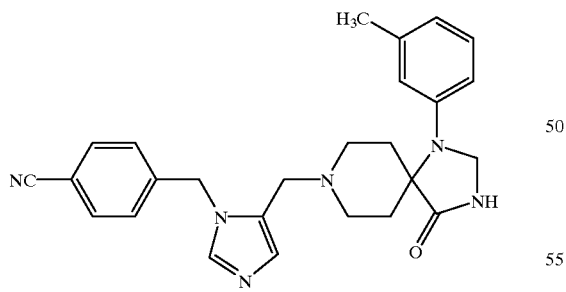

4-{5-[2-Oxo-1-(3-methylphenyl)-1,3,8-triaza-spiro[4.5]dec-8-ylmethyl]imidazol-1-ylmethyl]benzonitrile

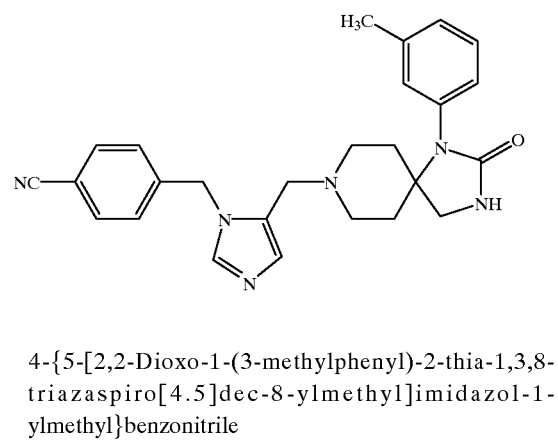

4-{5-[2,2-Dioxo-1-(3-methylphenyl)-2-thia-1,3,8-triazaspiro[4.5]dec-8-ylmethyl]imidazol-1-ylmethyl}benzonitrile

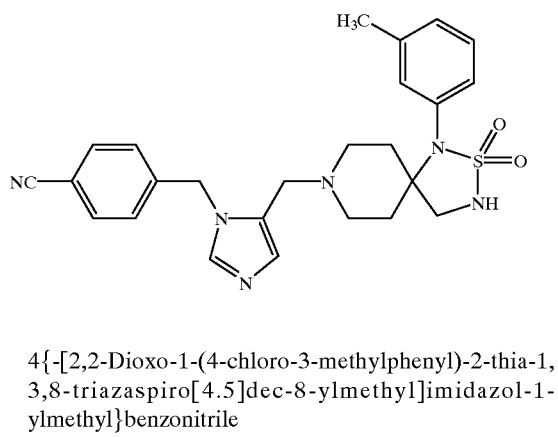

4{-[2,2-Dioxo-1-(4-chloro-3-methylphenyl)-2-thia-1,3,8-triazaspiro[4.5]dec-8-ylmethyl]imidazol-1-ylmethyl}benzonitrile

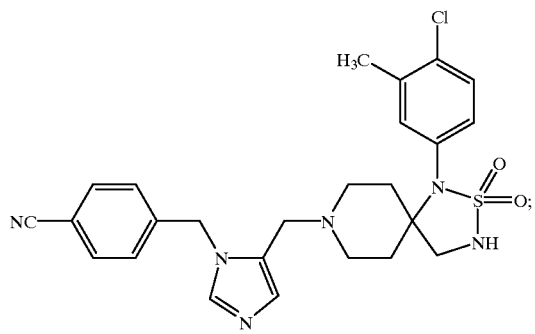

4-[5-(4-Oxo-3-(3-trifluoromethoxybenzyl)-1-phenyl-1,3,8-triazaspiro[4.5]dec-8-ylmethyl)imidazol-1-ylmethyl}benzonitrile

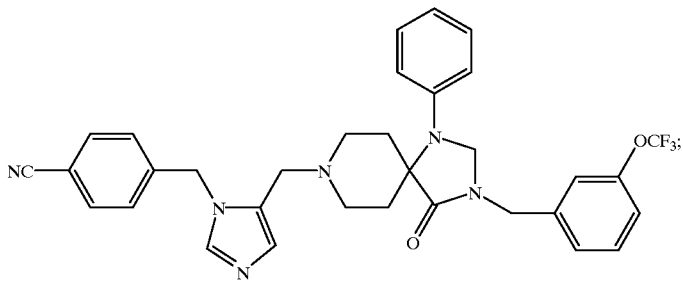

4-[5-(4-Oxo-3-(2-trifluoromethoxybenzyl)-1-phenyl-1,3,8-triazaspiro[4.5]dec-8-ylmethyl)imidazol-1-ylmethyl}benzonitrile

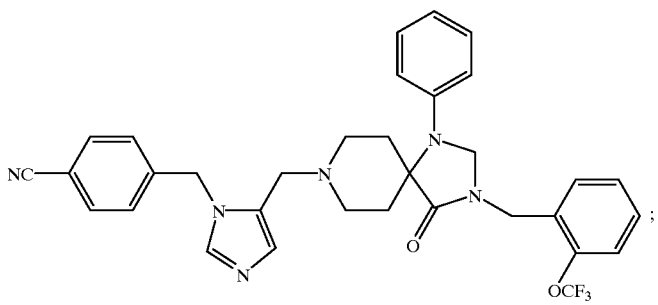

4-[5-(2-Oxo-3-(3-trifluoromethoxybenzyl)-1-oxa-3,8-diaza-spiro[4.5]dec-8-ylmethyl)imidazol-1-ylmethyl}benzonitrile

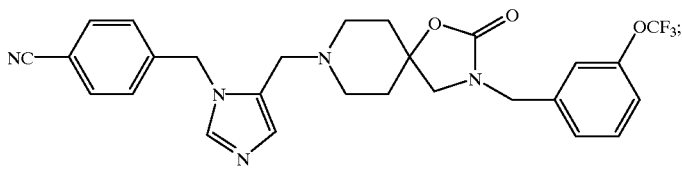

4-[5-(1,3-Dioxo-2-(3-trifluoromethoxybenzyl)-2,8-diaza-spiro[4.5]dec-8-ylmethyl)imidazol-1-ylmethyl}benzonitrile

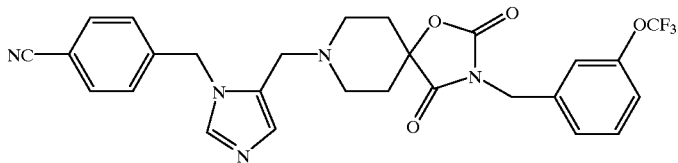

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^6$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic, which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of monocyclic and bicyclic heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, the terms "substituted aryl", "substituted heterocycle" and "substituted cycloalkyl" are intended to include the cyclic group containing from 1 to 3 substituents in addition to the point of attachment to the rest of the compound. Such substituents are preferably selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$, $(C_1-C_6 \text{ alkyl})OC(O)NH$— and $C_1-C_{20}$ alkyl.

Examples of the bicyclic moiety

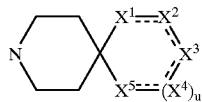

include, but are not limited to,

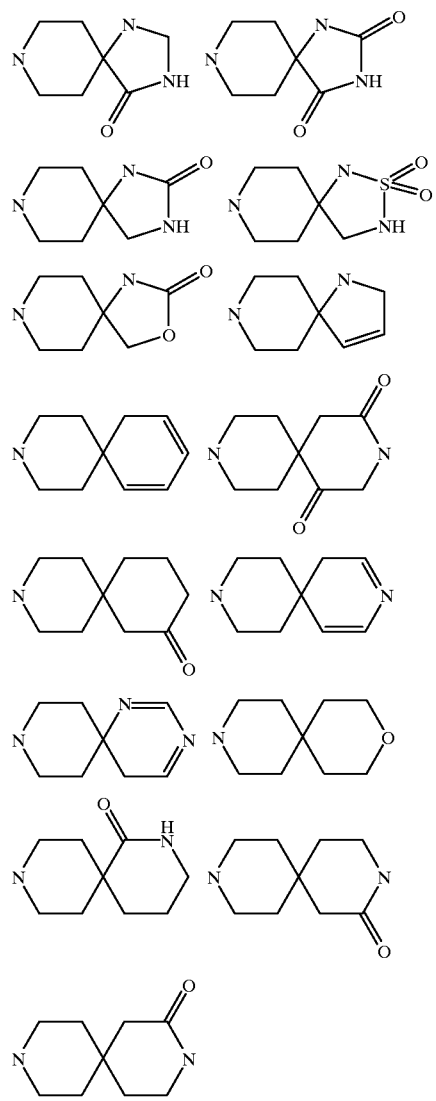

When $R^{4b}$ and $R^5$ or $R^{4a}$ and $R^{4b}$ are combined to form a ring, cyclic alkyl moieties are formed. Examples of such cyclic moieties include, but are not limited to,

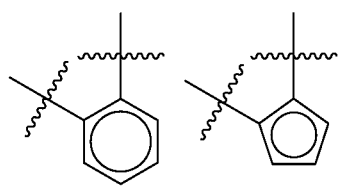

Examples of the bicyclic moiety when $R^{4b}$ and $R^5$ or $R^{4a}$ and $R^{4b}$ are combined to form a ring include, but are not limited to:

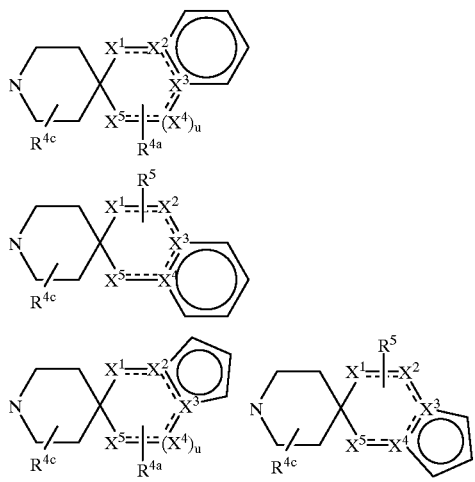

Specific examples of the tricyclic moieties include, but are not limited to,

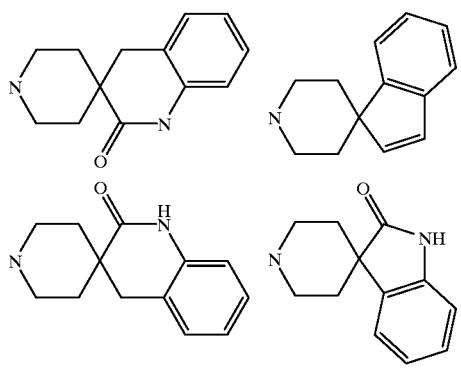

When $R^6$ and $R^7$ or $R^7$ and $R^{7a}$ are combined to form a ring, cyclic amine moieties are formed. Examples of such cyclic moieties include, but are not limited to:

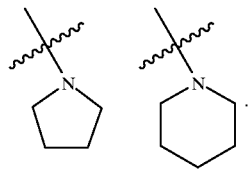

In addition, such cyclic moieties may optionally include another heteroatom(s). Examples of such heteroatom-containing cyclic amine moieties include, but are not limited to:

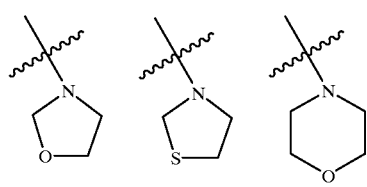

-continued

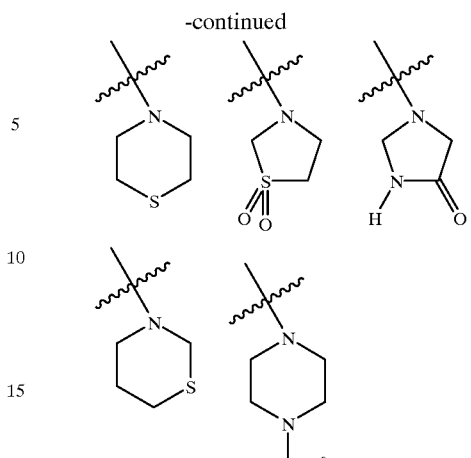

Lines drawn into the ring systems from substituents (such as from $R^2$, $R^{4a}$, $R^{4b}$, $R^5$, etc.) indicate that the indicated bond may be attached to any of the substitutable ring carbon or nitrogen atoms.

Preferably, $R^{1a}$ and $R^{1b}$ are independently selected from: hydrogen, $—N(R^8)_2$, $R^8C(O)NR^8—$ or $C_1$–$C_6$ alkyl which is unsubstituted or substituted by $—N(R^8)_2$, $R^8O—$ or $R^8C(O)NR^8—$.

Preferably, $R^1$ and $R^2$ is independently selected from: hydrogen, perfluoroalkyl, F, Cl, Br, $R^8O—$, $R^9S(O)_m—$, CN, $NO_2$, $R^8_2N—C(NR^8)—$, $R^8C(O)—$, $N_3$, $—N(R^8)_2$, $R^9OC(O)NR^8—$ and $C_1$–$C_6$ alkyl.

Preferably, $R^3$ is hydrogen or methyl.

Preferably, $R^{4a}$, $R^{4b}$ and $R^5$ are independently selected from:

a) C1-8 alkyl, unsubstituted or substituted with one or more of:
  1) aryl or heterocycle, unsubstituted or substituted with:
     i) $C_{1-4}$ alkyl,
     ii) $(CH_2)_pOR^6$,
     iii) $(CH_2)_pNR^6R^7$,
     iv) halogen,
     v) $C_{1-4}$ perfluoroalkyl,
  2) $OR^6$,
  3) $SR^6$, $S(O)R^6$, $SO^2R^6$, or
  4) 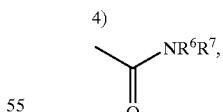
  b) 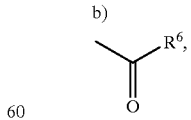

c) aryl, unsubstituted or substituted with one or more of:
  1) $C_{1-8}$ alkyl,
  2) $C_{1-8}$ perfluoroalkyl,
  3) halo,
  4) $OR^6$, 5) $SR^6$, $S(O)R^6$, $SO_2R^6$, or

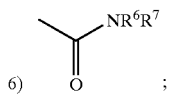

6)

d) —$SO2R^6$.

More preferably, $R^{4a}$, $R^{4b}$ or $R^5$ is selected from unsubstituted or substituted phenyl.

Preferably, $R^{4c}$ is hydrogen.

Preferably, $R^{7a}$ is $C_1$-$C_6$ alkyl substituted with hydrogen or an unsubstituted or substituted aryl group.

Preferably, $R^8$ is selected from H, $C_1$-$C_6$ alkyl and benzyl.

Preferably, $A^1$ and $A^2$ are independently selected from: a bond, —$C(O)NR^8$—, —$NR^8C(O)$—, O, —$N(R^8)$—, —$S(O)_2N(R^8)$— and —$N(R^8)S(O)_2$—.

Preferably, V is selected from hydrogen, heterocycle and aryl. More preferably, V is aryl or heterocycle. Most preferably, V is phenyl or pyridyl.

Preferably, W is imidazolyl.

Preferably, $X^2$ is $CH_2$, C=O or $S(O)_2$.

Preferably, $X^3$ is NH or O.

Preferably, $X^5$ is $CH_2$ or C=O.

Preferably, n, p and r are independently 0, 1, or 2. More preferably, r is 1.

Preferably t is 1.

Preferably, the moiety

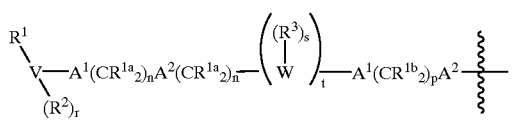

is selected from:

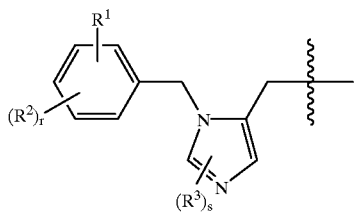

and

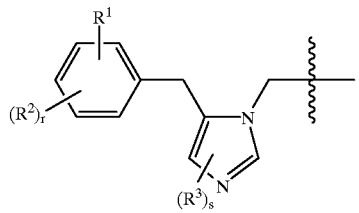

Preferably, the moiety:

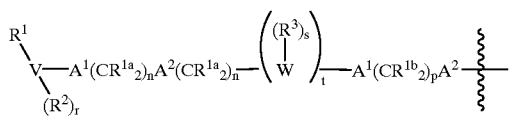

is attached to the nitrogen atom of the piperidinyl ring.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, n, etc.) at a particular location in a molecule be independent of its definitions elsewhere in that molecule. Thus, $N(R^8)_2$ represents —$NH_2$, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations used in the description of the chemistry and in the Examples that follow are:
$Ac_2O$ Acetic anhydride;
Boc t-Butoxycarbonyl;
$CB_z$ Carbobenzyloxy;
DBU 1,8-diazabicyclo[5.4.0]undec-7-ene;
DMAP 4-Dimethylaminopyridine;
DME 1,2-Dimethoxyethane;
DMF Dimethylformamide;
EDC 1-(3-dimethylaminopropyl)-3-ethyl-carbodiimide-hydrochloride;
$Et_3N$ Triethylamine;
EtOAc Ethyl acetate;
FAB Fast atom bombardment;
HOBT 1-Hydroxybenzotriazole hydrate;
HOOBT 3-Hydroxy-1,2,2-benzotriazin-4(3H)-one;
HPLC High-performance liquid chromatography;
MCPBA m-Chloroperoxybenzoic acid;
MsCl Methanesulfonyl chloride;
NaHMDS Sodium bis(trimethylsilyl)amide;
Py Pyridine;
TFA Trifluoroacetic acid;
THF Tetrahydrofuran.

The compounds of this invention are prepared by employing reactions as shown in Schemes 1–12, in addition to other standard manipulations such as ester hydrolysis, cleavage of protecting groups, etc., as may be known in the literature or exemplified in the experimental procedures. While stereochemistry is shown in the Schemes, a person of ordinary skill in the art would understand that the illustrated compounds represent racemic mixtures which may be separated at a subsequent purification step or may be utilized as the racemic mixture.

These reactions may be employed in a linear sequence to provide the compounds of the invention or they may be used to synthesize fragments which are subsequently joined by the reductive alkylation or acylation reactions described in the Schemes.

Schemes 12–15 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.
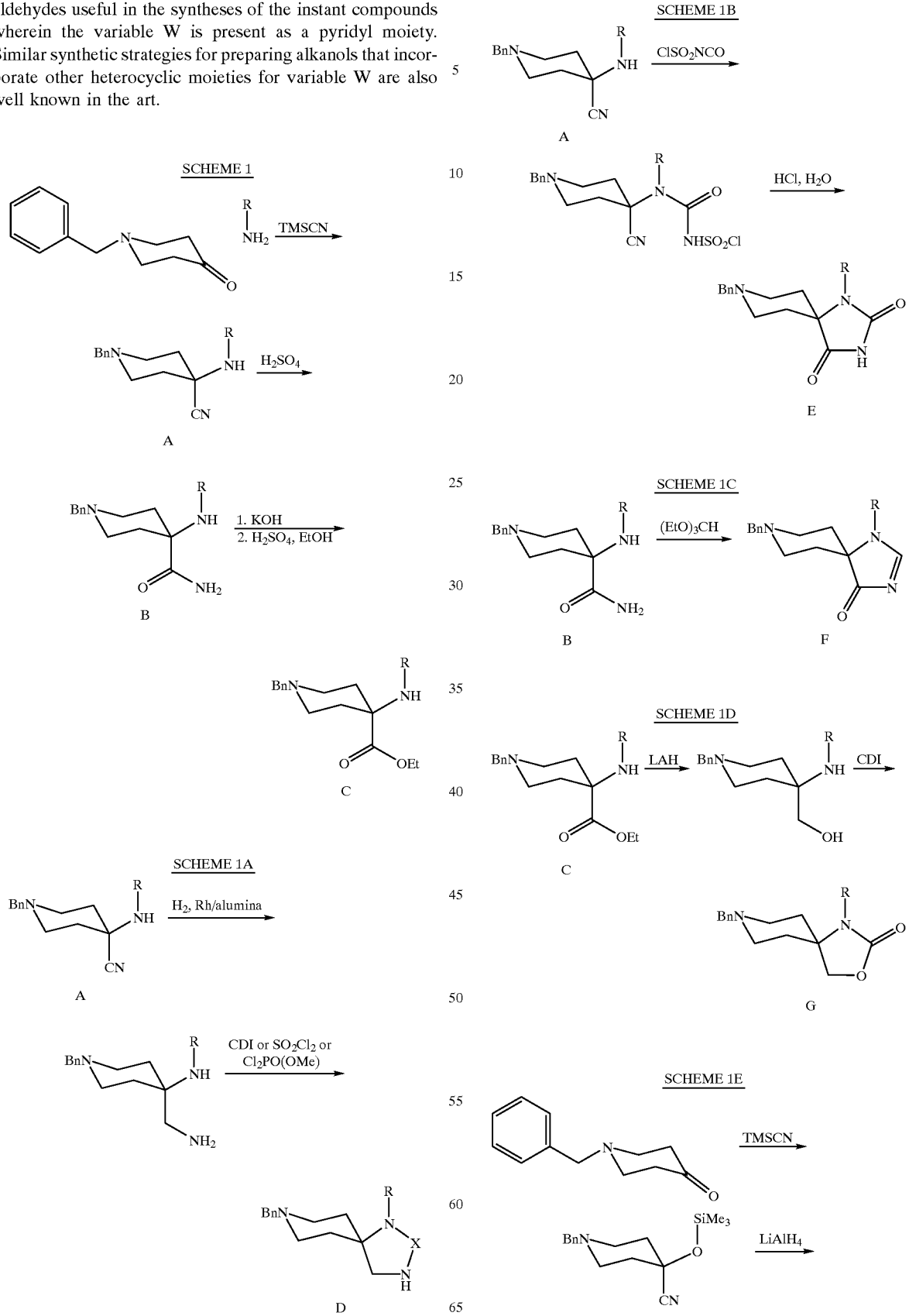

31
-continued
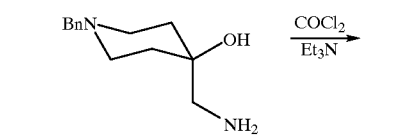
COCl₂
Et₃N
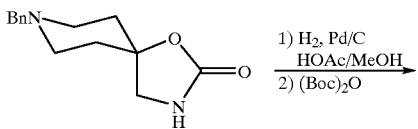
1) H₂, Pd/C
HOAc/MeOH
2) (Boc)₂O
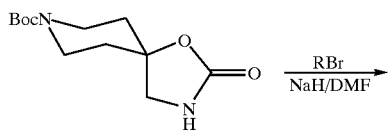
RBr
NaH/DMF
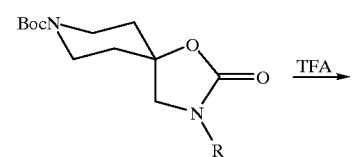
TFA
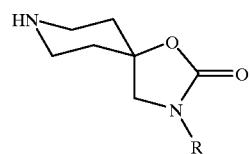
SCHEME 1F
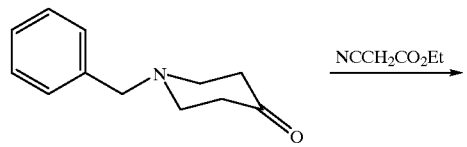
NCCH₂CO₂Et
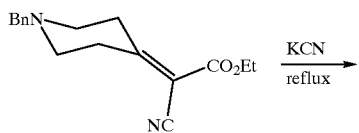
KCN
reflux
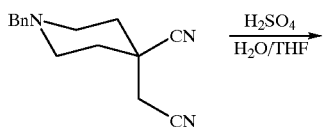
H₂SO₄
H₂O/THF
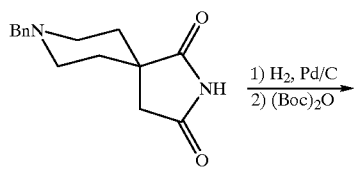
1) H₂, Pd/C
2) (Boc)₂O
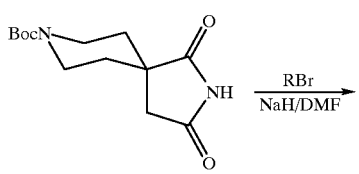
RBr
NaH/DMF
32
-continued
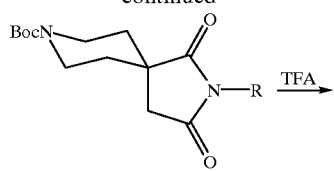
TFA
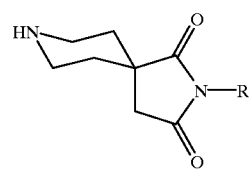
SCHEME 1G
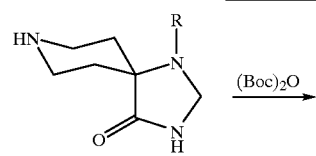
(Boc)₂O
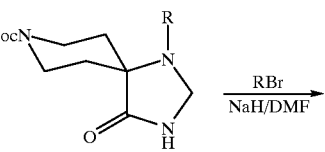
RBr
NaH/DMF
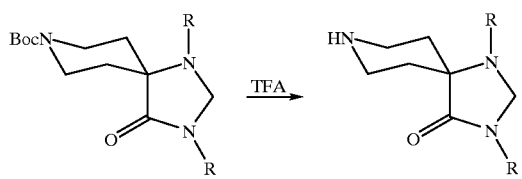
TFA
SCHEME 1H
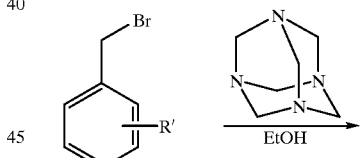
EtOH
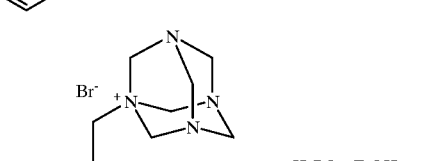
H₃PO₄, EtOH
C₂H₅COOH
—EtOCH₂OEt
—NH₄Br
-2 NH₄H₂PO₄
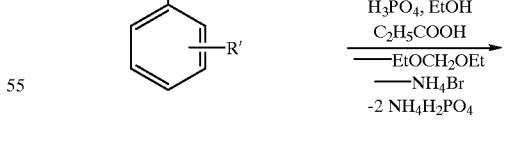
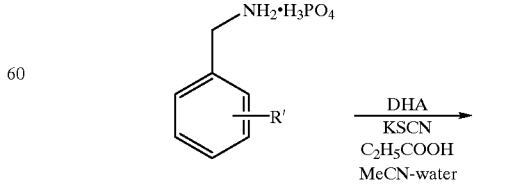
DHA
KSCN
C₂H₅COOH
MeCN-water

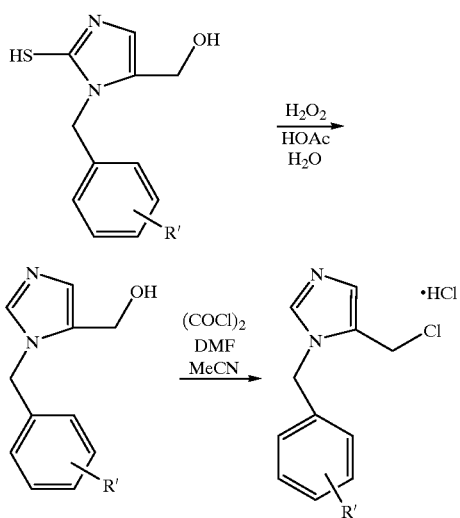
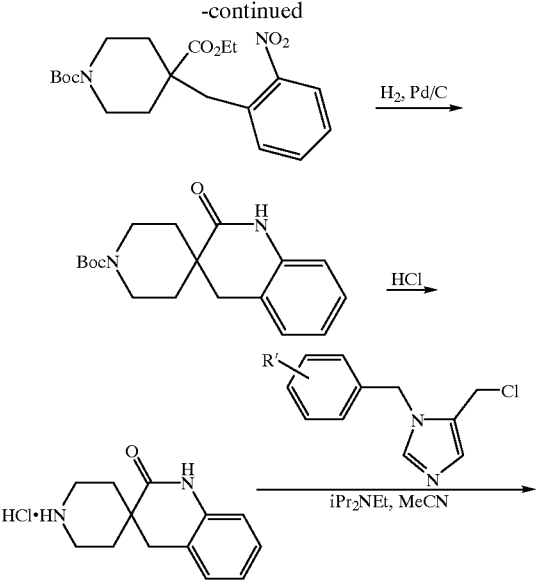
SCHEME 2
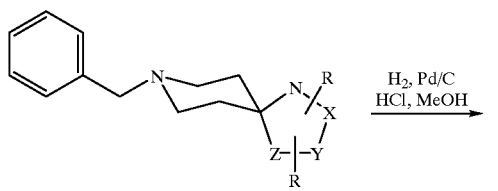
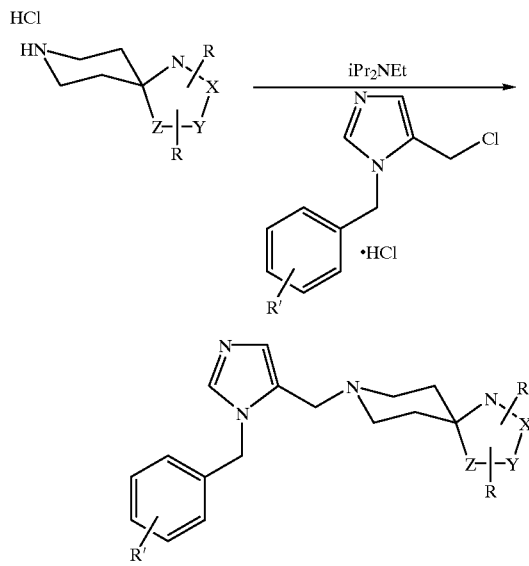
SCHEME 4
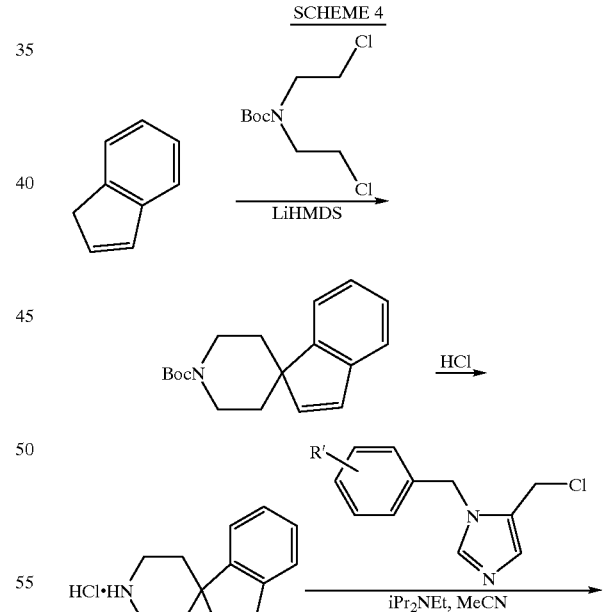
SCHEME 3
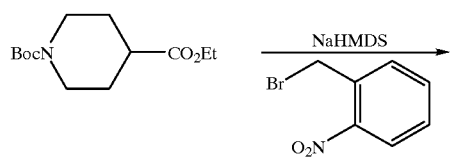

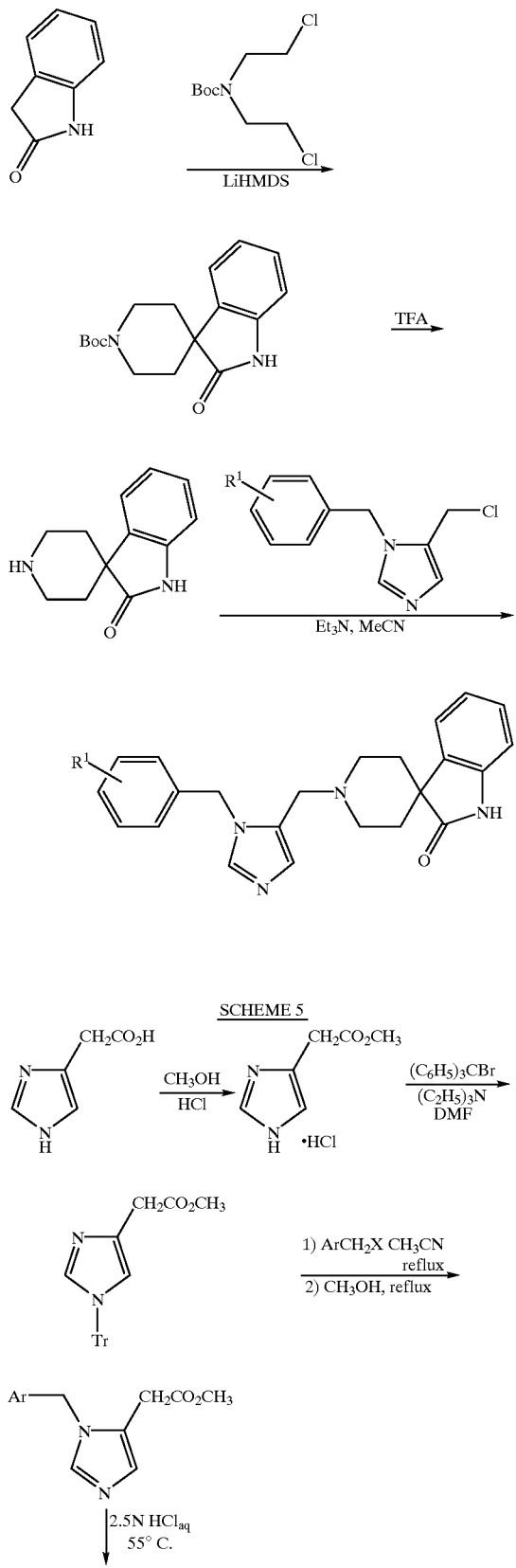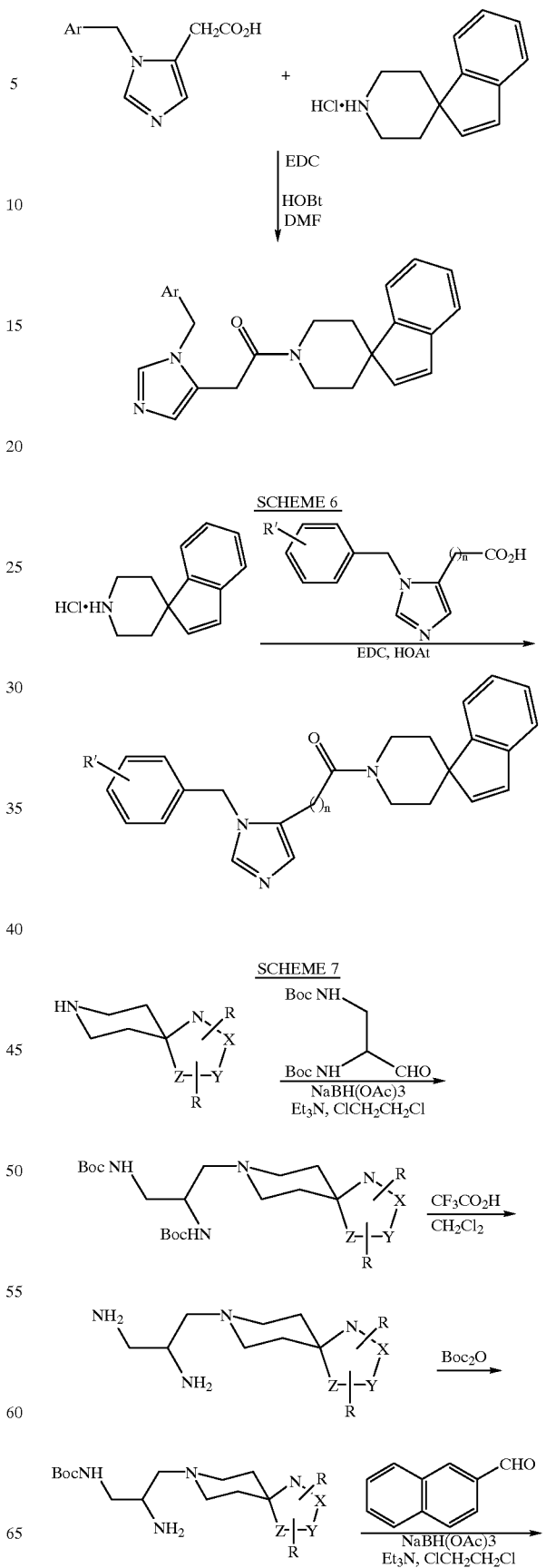

37
-continued
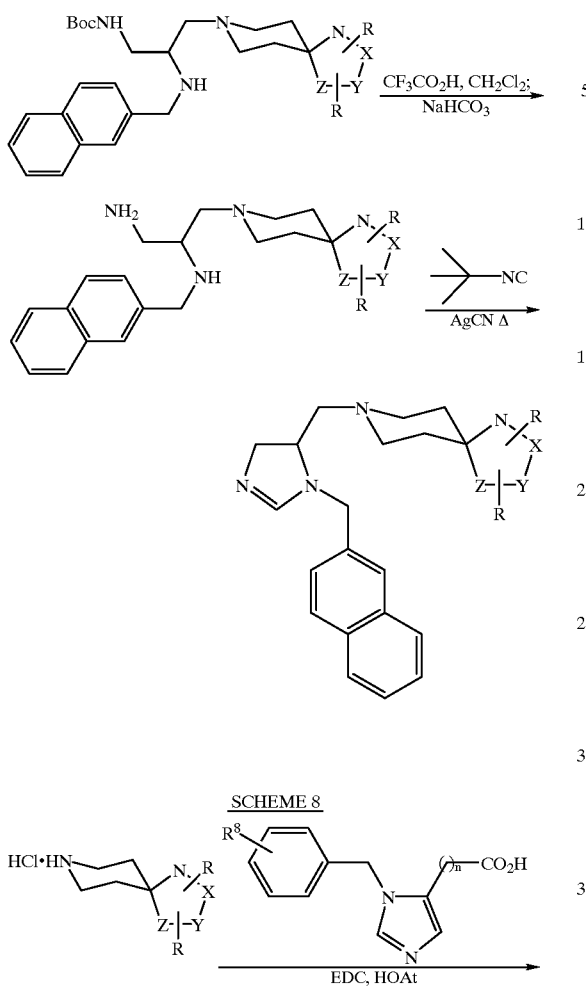
38
-continued
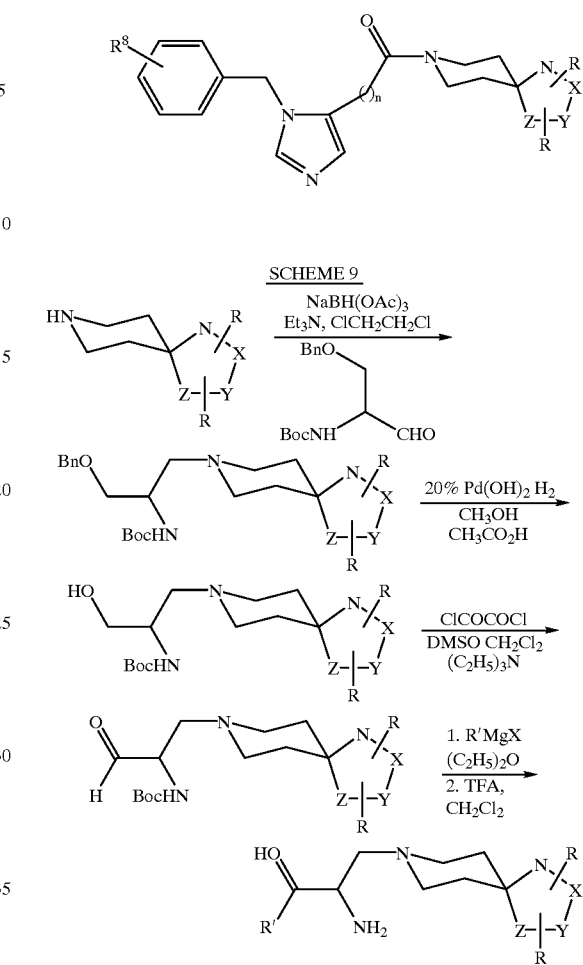
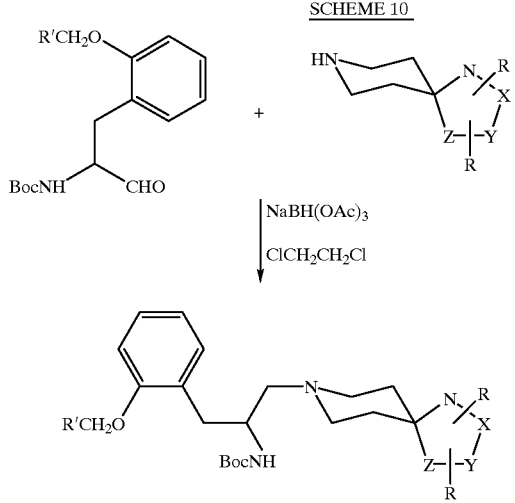

-continued
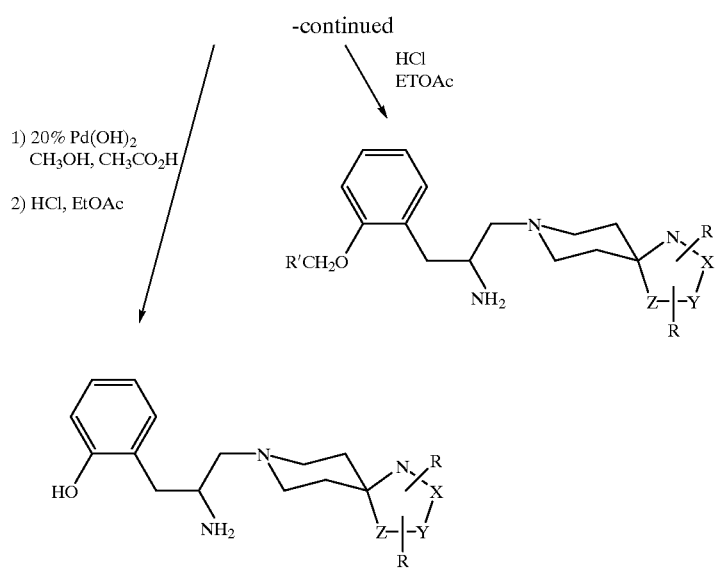
SCHEME 11
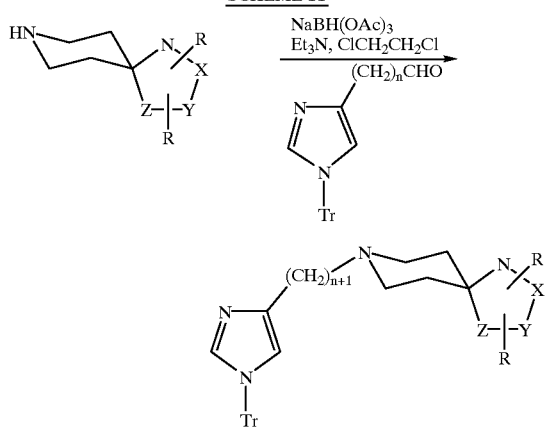
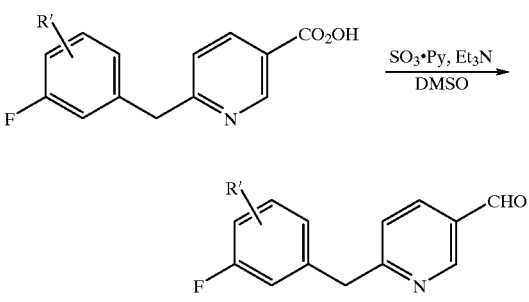
SCHEME 12
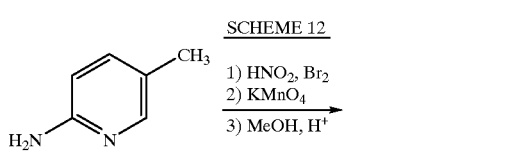
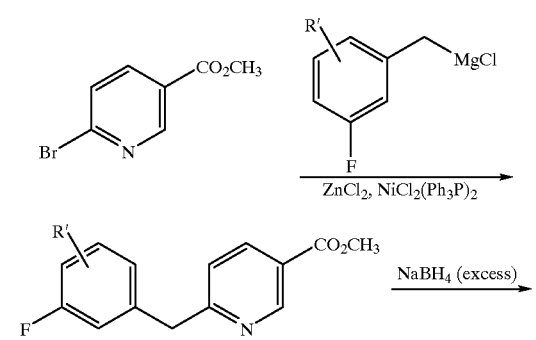
SCHEME 13
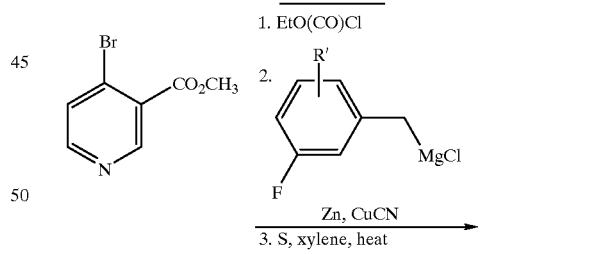
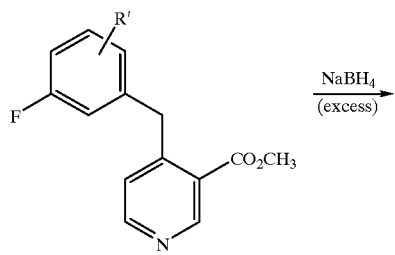

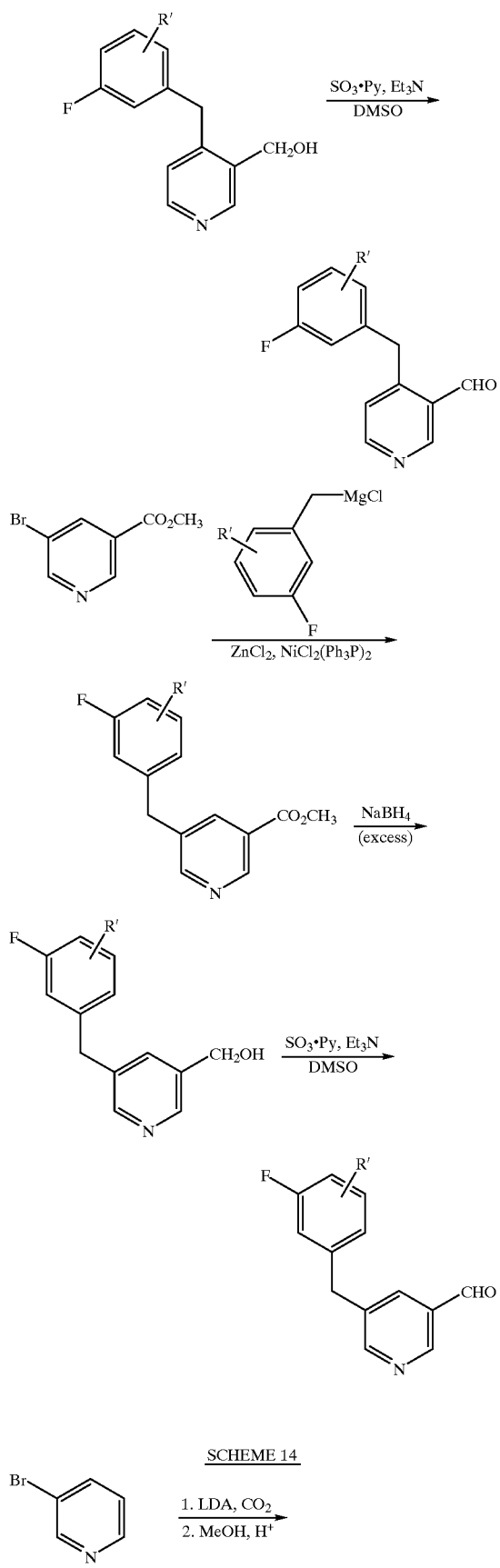
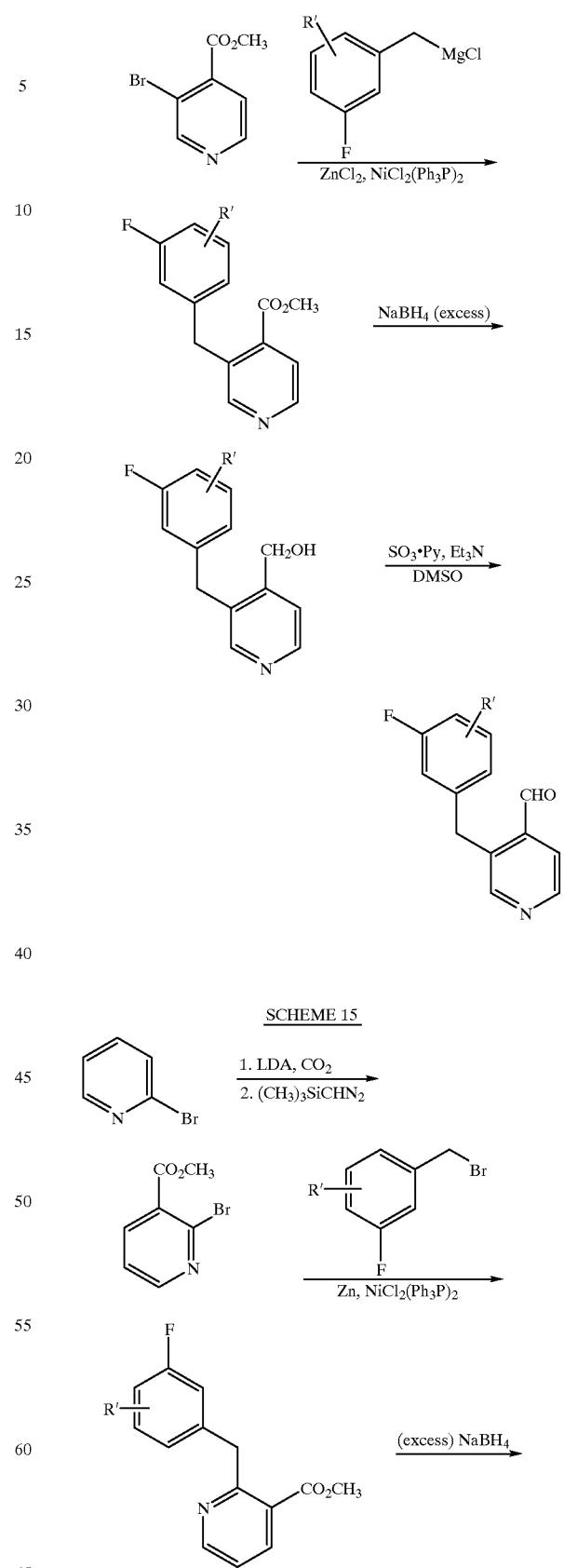
SCHEME 14
SCHEME 15

-continued

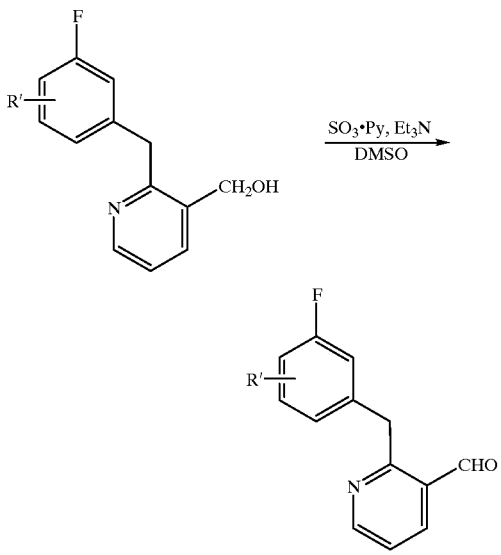

In the above Schemes, it is understood that

R is independently $R^{4a}$, $R^{4b}$ or $R^5$ or a protected precursor thereof, R' is independently $R^2$ or a protected precursor thereof, X, Y and Z are independently CH, $CH_2$, N or NH; and Ar is an unsubstituted or substituted aryl.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, ab1, lck, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the compounds are useful in the treatment of neurofibromatosis, which is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 19, is at least 100 times greater than the in vitro activity of the same compound against geranylgeranyl-protein transferase-type I in the assay described in Example 20. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

b) an $IC_{50}$ (a measure of in vitro inhibitory activity) for inhibition of the prenylation of newly synthesized K-Ras protein more than about 100-fold higher than the $IC_{50}$ for the inhibition of the farnesylation of hDJ protein.

When measuring such $IC_{50}$s the assays described in Examples 24 and 25 may be utilized.

It is also preferred that the selective inhibitor of farnesyl-protein transferase is further characterized by:

c) an $IC_{50}$ (a measurement of in vitro inhibitory activity) for inhibition of K4B-Ras dependent activation of MAP kinases in cells at least 100-fold greater than the $IC_{50}$ for inhibition of the farnesylation of the protein hDJ in cells.

It is also preferred that the selective inhibitor of farnesyl-protein transferase is further characterized by:

d) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 23 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Example 23, it is preferred that the dual inhibitor compound has an in vitro inhibitory activity ($IC_{50}$) that is less than about 12 $\mu$M against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 23.

In yet another embodiment, a compound of the instant invention may be a more potent inhibitor of geranylgeranyl-protein transferase-type I than it is an inhibitor of farnesyl-protein transferase.

As used herein, the term "composition" is intended to encompass a product comprising the specified ingredients in the specific amounts, as well as any product which results directly or indirectly, from combination of the specific ingredients in specified amounts.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

The compositions of the instant invention may alternatively or in addition comprise a farnesyl pyrophosphate-competitive inhibitor obtained by fermentation of cultures of novel organisms. In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well-known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

The compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that the instant combination of antineoplastic agent and inhibitor of prenyl-protein transferase may be used in conjunction with other methods of treating cancer and/or tumors, including radiation therapy and surgery.

Examples of an antineoplastic agent include, in general, microtubule-stabilising agents (such as paclitaxel (also known as Taxol®), docetaxel (also known as Taxotere®), or their derivatives); alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, trastuzumab (Herceptin™), 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, pyridobenzoindole derivatives, interferons and interleukins. Preferably, the antineoplastic agent is paclitaxel.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

Radiation therapy, including x-rays or gamma rays which are delivered from either an externally applied beam or by implantation of tiny radioactive sources, may also be used in combination with an inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 4-[5-(4-Oxo-1-phenyl-1,3,8-triazaspiro[4.5]dec-8-ylmethyl)imidazol-1-ylmethyl]benzonitrile

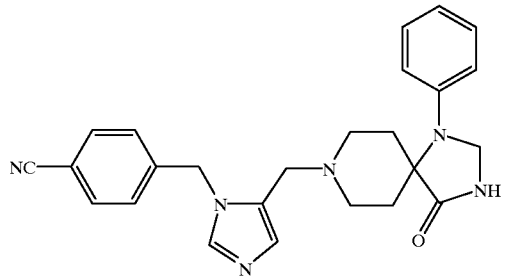

Step A:
Preparation of 1-(4-Cyanobenzyl)-5-chloromethylimidazole hydrochloride salt

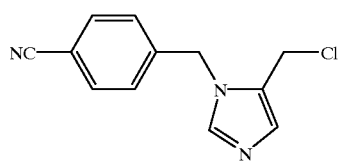

A mixture of 1-(4-cyanobenzyl)-5-hydroxymethylimidazole (10.8 g, 50.70 mmol) and thionyl chloride (70 mL, 960 mmol) was stirred at room temp. overnight under a calcium chloride drying tube. The resultant mixture was concentrated under vacuum, and residual thionyl chloride removed by co-evaporation with toluene.

The residue was recrystallized from boiling methanol. After cooling to room temp., the white solid precipitated was obtained by filtration, and residual solvent removed under vacuum overnight.

Alternate Step A:

Substep I: p-Cyanobenzylamine•H₃PO₄ salt

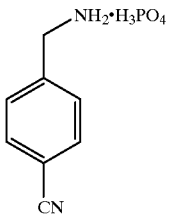

A slurry of HMTA in 2.5 L EtOH was added gradually over about 30 min to about 60 min to a stirred slurry of cyanobenzyl-bromide in 3.5 L EtOH and maintained at about 48–53° C. with heating & cooling in a 22L neck flask (small exotherm). Then the transfer of HMTA to the reaction mixture was completed with the use of 1.0 L EtOH. The reaction mixture was heated to about 68–73° C. and aged at about 68–73° C. for about 90 min. The reaction mixture was a slurry containing a granular precipitate which quickly settled when stirring stopped.

The mixture was cooled to a temperature of about 50° C. to about 55° C. Propionic acid was added to the mixture and the mixture was heated and maintained at a temperature of about 50° C. to about 55° C. Phosphoric acid was gradually added over about 5 min to about 10 min, maintaining the reaction mixture below about 65° C. to form a precipitate-containing mixture. Then the mixture was gradually warmed to about 65° C. to about 70° C. over about 30 min and aged at about 65° C. to about 70° C. for about 30 min. The mixture was then gradually cooled to about 20–25° C. over about 1 hour and aged at about 20–25° C. for about 1 hour.

The reaction slurry was then filtered. The filter cake was washed four times with EtOH, using the following sequence, 2.5 L each time. The filter cake was then washed with water five times, using 300 mL each time. Finally, the filter cake was washed twice with MeCN (1.0 L each time) and the above identified compound was obtained.

Substep II: 4-Cyanobenzylamine Hydrochloride via Hexamethylene-tetrammonium salt

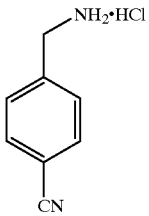

A 72 liter vessel was charged with 190 proof ethanol (14.4 L) followed by the addition of 4-cyanobenzylbromide (2.98 kg) and HMTA (2.18 kg) at ambient temperature. The mixture was heated to about 72–75° C. over about 60 min. On warming, the solution thickens and additional ethanol (1.0 liter) was added to facilitate stirring. The batch was aged at about 72–75° C. for about 30 min.

The mixture was allowed to cool to about 20° C. over about 60 min, and HCl gas (2.20 kg) was sparged into the slurry over about 4 hours during which time the temperature rose to about 65° C. The mixture was heated to about 70–72° C. and aged for about 1 hour. The slurry was cooled to about 30° C. and ethyl acetate (22.3 L) added over about 30 min. The slurry was cooled to about −5° C. over about 40 min and aged at about −3 to about −5° C. for about 30 min. The mixture was filtered and the crystalline solid was washed with chilled ethyl acetate (3×3 L). The solid was dried under a N₂ stream for about 1 hour before charging to a 50 liter vessel containing water (5.5 L). The pH was adjusted to about 10–10.5 with 50% NaOH (4.0 kg) maintaining the internal temperature below about 30° C. At about 25° C., methylene chloride (2.8 L) was added and stirring continued for about 15 min. The layers were allowed to settle and the lower organic layer was removed. The aqueous layer was extracted with methylene chloride (2×2.2 L). The combined organic layers were dried over potassium carbonate (650 g). The carbonate was removed via filtration and the filtrate concentrated in vacuo at about 25° C. to give a free base as a yellow oil.

The oil was transferred to a 50 liter vessel with the aid of ethanol (1.8 L). Ethyl acetate (4.1 L) was added at about 25° C. The solution was cooled to about 15° C. and HCl gas (600 g) was sparged in over about 3 hours, while keeping batch temperature below about 40° C. At about 20–25° C., ethyl acetate (5.8 L) was added to the slurry, followed by cooling to about −5° C. over about 1 hour. The slurry was aged at about −5° C. for about 1 hour and the solids isolated via filtration. The cake was washed with a chilled mixture of EtOAc/EtOH (9:1 v/v) (1×3.8 L), then the cake was washed with chilled EtOAc (2×3.8 L). The solids were dried in vacuo at about 25° C. to provide the above-titled compound.

¹H NMR (250 MHz, CDCl₃) δ 7.83–7.79 (d, 2H), 7.60–7.57 (d, 2H), 4.79 (s, 2H), 4.25 (s, 2H); ¹³C NMR (62.9 MHz, CDCl₃) δ 149.9, 139.8, 134.2, 131.2, 119.7, 113.4, 49.9, 49.5, 49.2, 48.8, 48.5, 48.2, 43.8.

Substep III: 1-(4-Cyanobenzyl)-2-Mercapto-5-Hydroxymethyl-imidazole

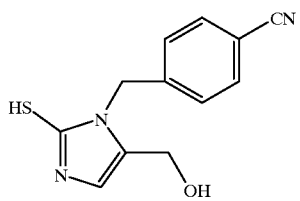

7% water in acetonitrile (50 mL) was added to a 250 mL roundbottom flask. Next, an amine phosphate salt (12.49 g), as described above in Substep I, was added to the flask. Next potassium thiocyanate (6.04 g) and dihydroxyacetone (5.61 g) was added. Lastly, propionic acid (10.0 mL) was added. Acetonitrile/water 93:7 (25 mL) was used to rinse down the sides of the flask. This mixture was then heated to 60° C., aged for about 30 minutes and seeded with 1% thioimidazole. The mixture was then aged for about 1.5 to about 2 hours at 60° C. Next, the mixture was heated to 70° C., and aged for 2 hours. The temperature of the mixture was then cooled to room temperature and was aged overnight. The thioimidazole product was obtained by vacuum filtration. The filter cake was washed four times acetonitrile (25 mL each time) until the filtrates became nearly colorless. Then the filter cake was washed three times with water (approximately 25–50 mL each time) and dried in vacuo to obtain the above-identified compound.

Substep IV: 1-(4-Cyanobenzyl)-5-Hydroxymethylimidazole

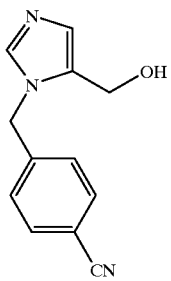

A 1L flask with cooling/heating jacket and glass stirrer (Lab-Max) was charged with water (200 mL) at 25° C. The thioimidazole (90.27 g), as described above in Substep III, was added, followed by acetic acid (120 mL) and water (50 mL) to form a pale pink slurry. The reaction was warmed to 40° C. over 10 minutes. Hydrogen peroxide (90.0 g) was added slowly over 2 hours by automatic pump maintaining a temperature of 35–45° C. The temperature was lowered to 25° C. and the solution aged for 1 hour.

The solution was cooled to 20° C. and quenched by slowly adding 20% aqueous $Na_2SO_3$ (25 mL) maintaining the temperature at less than 25° C. The solution was filtered through a bed of DARCO G-60 (9.0 g) over a bed of SolkaFlok (1.9 g) in a sintered glass funnel. The bed was washed with 25 mL of 10% acetic acid in water.

The combined filtrates were cooled to 15° C. and a 25% aqueous ammonia was added over a 30 minute period, maintaining the temperature below 25° C., to a pH of 9.3. The yellowish slurry was aged overnight at 23° C. (room temperature). The solids were isolated via vacuum filtration. The cake (100 mL wet volume) was washed with 2×250 mL 5% ammonia (25%) in water, followed by 100 mL of ethyl acetate. The wet cake was dried with vacuum/$N_2$ flow and the above-titled compound was obtained.

$^1$H NMR (250 MHz, $CDCl_3$): δ 7.84–7.72 (d, 2H), 7.31–7.28 (d, 2H), 6.85 (s, 1H), 5.34 (s, 2H), 5.14–5.11 (t, 1H), 4.30–4.28 (d, 2H), 3.35 (s, 1H).

Substep V: 1-(4-cyanobenzyl)-5-chloromethyl imidazole HCl salt

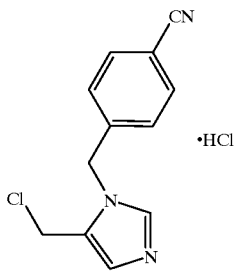

1-(4-Cyanobenzyl)-5-hydroxymethylimidazole (1.0 kg), as described in above in Substep IV, was slurried with DMF (4.8 L) at 22° C. and then cooled to −5° C. Thionyl chloride (390 mL) was added dropwise over 60 min during which time the reaction temperature rose to a maximum of 9° C. The solution became nearly homogeneous before the product began to precipitate from solution. The slurry was warmed to 26° C. and aged for 1 h.

The slurry was then cooled to 5° C. and 2-propanol (120 mL) was added dropwise, followed by the addition of ethyl acetate (4.8 L). The slurry was aged at 5° C. for 1 h before the solids were isolated and washed with chilled ethyl acetate (3×1 L). The product was dried in vacuo at 40° C. overnight to provide the above-titled compound.

$^1$H NMR (250 MHz DMSO-$d_6$): δ 9.44 (s, 1H), 7.89 (d, 2H, 8.3 Hz), 7.89 (s, 1H), 7.55 (d, 2H, 8.3 Hz), 5.70 (s, 2H), 4.93 (s, 2H). $^{13}$C NMR (75.5 MHz DMSO-$d_6$): $δ_c$ 139.7, 137.7, 132.7, 130.1, 128.8, 120.7, 118.4, 111.2, 48.9, 33.1.

Substep VI: 1-(4-Cyanobenzyl)-5-Chloromethyl Imidazole HCl salt via addition of Hydroxymethylimidazole to Vilsmeier Reagent

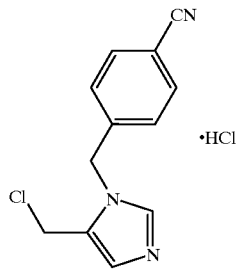

To an ice cold solution of dry acetonitrile (3.2 L, 15 L/Kg hydroxymethylimidazole) was added 99% oxalyl chloride (101 mL, 1.15 mol, 1.15 equiv.), followed by dry DMF (178 mL, 2.30 mol, 2.30 equiv.), at which time vigorous evolution of gas was observed. After stirring for about 5 to 10 min following the addition of DMF, solid hydroxymethylimidazole (213 g, 1.00 mol), as described above in Substep IV, was added gradually. After the addition, the internal temperature was allowed to warm to a temperature of about 23° C. to about 25° C. and stirred for about 1 to 3 hours. The mixture was filtered, then washed with dry acetonitrile (400 mL displacement wash, 550 mL slurry wash, and a 400 mL displacement wash). The solid was maintained under a $N_2$ atmosphere during the filtration and washing to prevent hydrolysis of the chloride by adventitious $H_2O$. This yielded the crystalline form of the chloromethylimidazole hydrochloride.

$^1$H NMR (250 MHz DMSO-$d_6$): δ 9.44 (s, 1H), 7.89 (d, 2H, 8.3 Hz), 7.89 (s, 1H), 7.55 (d, 2H, 8.3 Hz), 5.70 (s, 2H), 4.93 (s, 2H). $^{13}$C NMR (75.5 MHz DMSO-$d_6$): $δ_c$ 139.7, 137.7, 132.7, 130.1, 128.8, 120.7, 118.4, 111.2, 48.9, 33.1.

Substep VII: 1-(4-Cyanobenzyl)-5-Chloromethyl Imidazole HCl salt via addition of Vilsmeier Reagent to Hydroxymethylimidazole

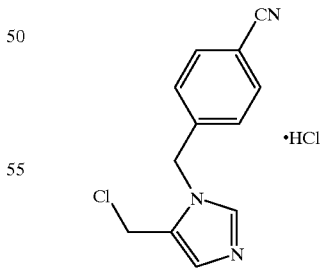

To an ice cold solution of dry DMF (178 mL, 2.30 mol, 2.30 equiv.) in dry acetonitrile (2.56 L, 12 L/Kg Hydroxymethylimidazole) was added oxalyl chloride (101 mL, 1.15 mol, 1.15 equiv). The heterogeneous mixture in the reagent vessel was then transferred to a mixture of hydroxymethylimidazole (213 g, 1.00 mol), as described above inSubstep IV, in dry acetonitrile (1.7 L, 8 L/Kg hydroxymethylimidazole). Additional dry acetonitrile (1.1–2.3 L, 5–11 L/Kg hydroxymethylimidazole) was added to the remaining solid Vilsmeier reagent in the reagent vessel. This, now nearly homogenous, solution was transferred to the reaction vessel at $T_i \leq +6°$ C. The reaction vessel temperature was warmed to a temperature of about 23° C. to about 25° C. and stirred for about 1 to 3 hours. The mixture was then cooled to 0° C. and aged 1 h. The solid was filtered and washed with dry, ice cold acetonitrile (400 mL displacement wash, 550 mL slurry wash, and a 400 mL displacement wash). The solid was maintained under a $N_2$ atmosphere during the filtration and washing to prevent hydrolysis of the chloride by adventitious $H_2O$. This yielded the crystalline form of the chloromethylimidazole hydrochloride.

Step B:

Preparation of 4-[5-(4-Oxo-1-phenyl-1,3,8-triazaspiro[4.5]-dec-8-ylmethyl)imidazol-1-ylmethyl]benzonitrile

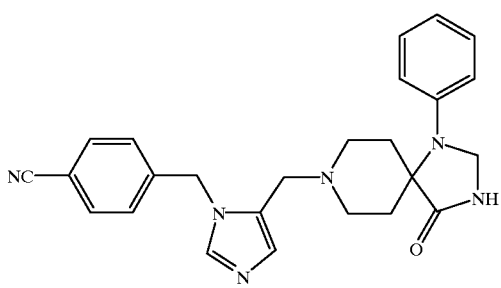

A solution of 1-phenyl-1,3,8-triazaspiro[4.5]decan-4-one (230 mg, 1 mmol), 1-(4-cyanobenzyl)-5-chloromethylimidazole hydrochloride salt (265 mg, 1 mmol), and diisopropylethylamine (0.52 mL, 3 mmol) in anhydrous acetonitrile (5 mL) was stirred at room temp. for 2 days. The resulting mixture was concentrated under vacuum, and the residue was subjected to column chromatography on silica gel eluting with 5% methanol in ethyl acetate. The appropriate fractions were collected and concentrated. The residue was triturated with diethyl ether, and the white solid precipitated was collected by filtration to provide the title compound.

Anal. Calcd for $C_{27}H_{28}N_4O_3 \cdot 0.25$ $Et_2O \cdot 0.7$ $H_2O$: C, 68.24; H, 6.59; N, 18.36. Found: C, 68.20; H, 6.33; N, 18.39.

Example 2

Preparation of 4-{5-[4-Oxo-1-(3-methylphenyl)-1,3,8-triazaspiro[4.5]dec-8-ylmethyl]imidazol-1-ylmethyl}benzonitrile

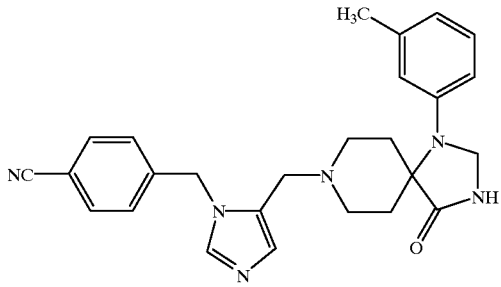

Step A:

Preparation of 1-Benzyl-4-cyano-4-(3-methylphenylamino)-piperidine

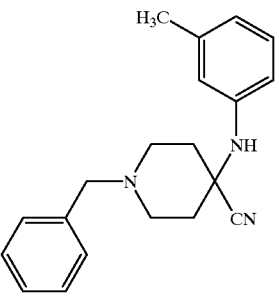

To a solution of 1-benzyl-4-piperidone (18.9 g, 0.1 mol) and 3-methylaniline (10.7 g, 0.1 mol) in glacial acetic acid (100 mL), trimethylsilyl cyanide (6.7 mL, 0.1 mol; Journal of Organic Chemistry, vol. 55, page 4207, year 1990) was added dropwise with the temp. of the reaction maintained <40° C. with an ice-water bath. After addition was complete, the reaction mixture was stirred at room temp. for 30 min, and poured into a mixture of ice (140 g) and concentrated ammonium hydroxide (168 g). The resultant mixture was extracted with chloroform (3 times). The organic extract was washed with brine, dried over anhydrous sodium sulfate, filtered, and concentrated under vacuum. The residual oil was triturated with diisopropyl ether (300 mL) and stirred at room temp. overnight. The white solid precipitated was filtered to provide the title compound.

Step B:

Preparation of 1-Benzyl-4-(3-methylphenylamino)-isonipecotamide

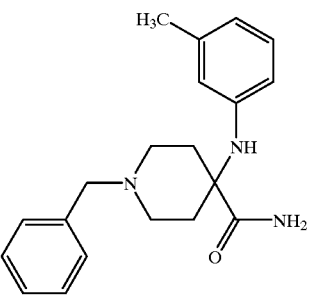

A mixture of 1-benzyl-4-cyano-4-(3-methylphenylamino)-piperidine (7.6 g) and 90% sulfuric acid (53 mL) was heated at 70° C. until all the solid dissolved (~1 h). The resultant mixture was stirred at the temp. for 30 min., and poured into a mixture of ice (80 g) and concentrated ammonium hydroxide (75 g). The solution was basified with ammonium hydroxide, and extracted with chloroform. The organic extract was washed with brine, dried over anhydrous sodium sulfate, filtered, and concentrated under vacuum to provide the title compound.

Step C:

Preparation of 8-Benzyl-1-(3-methylphenyl)-1,3,8-triazaspiro[4.5]dec-2-en-4-one

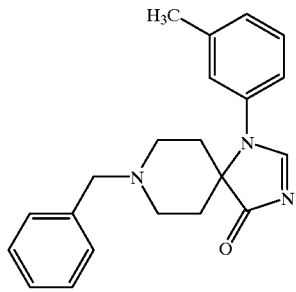

To a mixture of 1-benzyl-4-(3-methylphenylamino)-isonipecotamide (4.3 g, 13.5 mmol) and glacial acetic acid (1.0 mL) in toluene (20 mL) heated under reflux, triethyl orthoformate (2.0 g, 13.5 mmol) was added over a period of 3 h using a syringe pump. The resultant mixture was refluxed for 38 h., and treated with a mixture of concentrated ammonium hydroxide (1.3 mL) and water (3.4 mL). The organic extract was isolated, washed with brine, dried over anhydrous sodium sulfate, filtered, and concentrated. The residue was subjected to column chromatography on silica gel eluting with 5% methanol in chloroform. Collection and concentration of appropriate fractions provided the title compound.

Step D:

Preparation of 1-(3-Methylphenyl)-1,3,8-triazaspiro[4.5]-decan-4-one

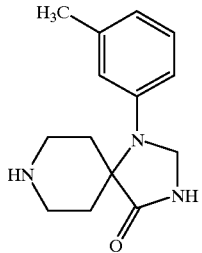

A mixture of 8-benzyl-1-(3-methylphenyl)-1,3,8-triazaspiro[4.5]dec-2-en-4-one (1.64 g, 4.9 mmol) and 10% palladium on charcoal (0.8 g) in a mixture of methanol (100 mL) and methanol saturated with anhydrous hydrochloride gas (5 mL) was shaken in a Parr hydrogenator at 55 psi for 24 h. The resultant mixture was filtered through a plug of Celite, and the filtrate concentrated under vacuum. The residue was subjected to column chromatography on silica gel eluting with a 1:1 mixture of 10% methanol in chloroform and chloroform saturated with ammonia gas. Collection and concentration of appropriate fractions provide the title compound.

Step E:

Preparation of 4-{5-[4-Oxo-1-(3-methylphenyl)-1,3,8-triazaspiro[4.5]dec-8-ylmethyl]imidazol-1-ylmethyl}benzonitrile

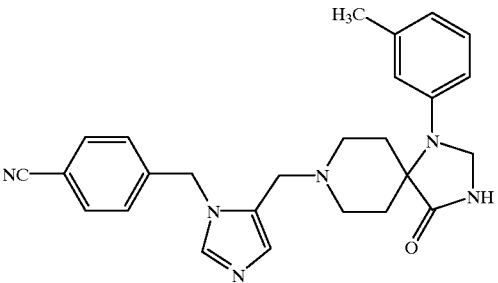

A solution of 1-(3-methylphenyl)-1,3,8-triazaspiro[4.5] decan-4-one (0.25 g, 0.94 mmol), 1-(4-cyanobenzyl)-5-chloromethylimidazole hydrochloride salt (0.23 g, 0.94 mmol), and diisopropylethylamine (0.5 mL, 2.8 mmol) in absolute ethanol (5 mL) was heated under reflux overnight. The resulting mixture was concentrated under vacuum, and the residue was subjected to column chromatography on silica gel eluting with 5% methanol in ethyl acetate. The appropriate fractions were collected and concentrated. The residue was triturated with diethyl ether, and the white solid precipitated was collected by filtration to provide the title compound.

Anal. Calcd for $C_{26}H_{28}N_6O \cdot 0.55$ MeOH: C, 69.60; H, 6.64; N, 18.34. Found: C, 69.60; H, 6.53; N, 18.11.

Example 3

Preparation of 4-{5-[4-Oxo-1-(4-methylphenyl)-1,3,8-triazaspiro[4.5]dec-8-ylmethyl]imidazol-1-ylmethyl}benzonitrile

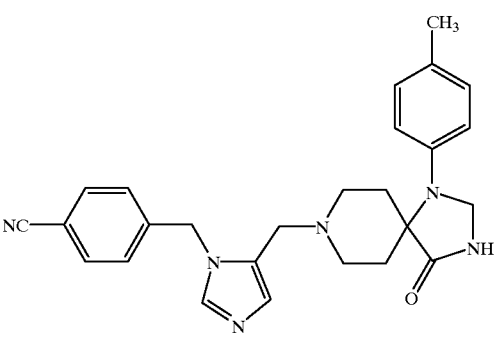

The title compound was prepared using the protocol described in Example 2, Steps A–E, substituting 3-methylaniline with 4-methylaniline in Step A.

Anal. Calcd for $C_{26}H_{28}N_6O$: C, 70.89; H, 6.41; N, 19.08. Found: C, 70.62; H, 6.21; N, 18.88.

Example 4

Preparation of 4-{5-[2,4-Dioxo-1-(3-methylphenyl)-1,3,8-triazaspiro[4.5]dec-8-ylmethyl]imidazol-1-ylmethyl}benzonitrile

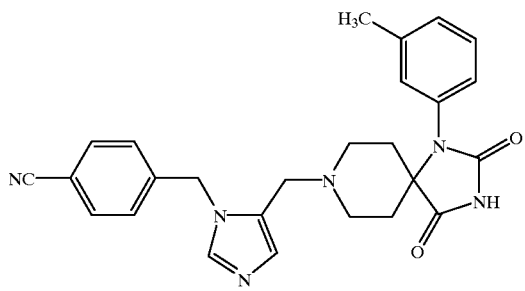

Step A:

Preparation of 8-Benzyl-1-(3-methylphenyl)-1,3,8-triazaspiro[4.5]decan-2,4-dione

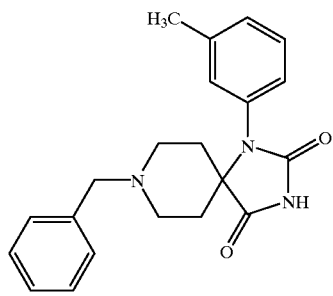

To a solution of 1-benzyl-4-cyano-4-(3-methylphenylamino)-piperidine (4.54 g, 14.86 mmol) as described above in Example 2, Step A) in dichloromethane (50 mL), a solution of chlorosulfonyl isocyanate (1.45 mL, 16.7 mmol; Journal of Organic Chemistry, vol. 55, page 4207, 1990) in dichloromethane (20 mL) was added slowly with the temperature of the reaction maintained between 20–30° C. The resultant white slurry was stirred at room temp. for 30 min, and concentrated under vacuum. The residue was treated with hydrochloric acid (50 mL, 1 M) and heated under reflux for 1 h. The resultant mixture was cooled to 0° C., and basified with aqueous sodium hydroxide (5 M) to pH 5.5. The solid precipitated was obtained by filtration, and further purified by column chromatography on silica gel eluting with 10% methanol in chloroform saturated with ammonia gas. Collection and concentration of appropriate fractions provided the title compound as white solid.

Step B:

Preparation of 4-{5-[2,4-Dioxo-1-(3-methylphenyl)-1,3,8-triaza-spiro[4.5]dec-8-ylmethyl]imidazol-1-ylmethyl}-benzonitrile

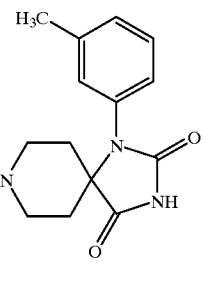

The title compound was prepared using the protocol described in Example 2, Steps D–E, substituting 8-benzyl-1-(3-methylphenyl)-1,3,8-triaza-spiro[4.5]dec-2-en-4-one with 8-benzyl-1-(3-methylphenyl)-1,3,8-triaza-spiro[4.5]decan-2,4-dione in used Step D. Anal. Calcd for $C_{26}H_{26}N_6O_2$: C, 67.97; H, 5.94; N, 18.02. Found: C, 67.91; H, 5.79; N, 18.00.

Example 5

Preparation of 4-{5-[2-Oxo-1-(3-methylphenyl)-1,3,8-triaza-spiro[4.5]dec-8-ylmethyl]imidazol-1-ylmethyl}benzonitrile

Step A:

Preparation of 1-Benzyl-4-(3-methylphenylamino)-4-aminomethylpiperidine

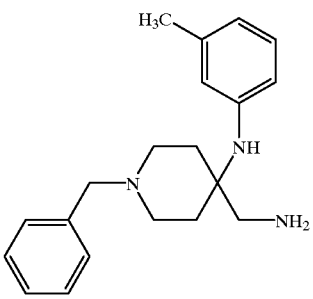

A mixture of 1-benzyl-4-cyano-4-(3-methylphenylamino)-piperidine (4.0 g), as described above in Example 2, Step A, and 5% rhodium on alumina (4 g) in absolute ethanol (100 mL) treated with anhydrous ammonia gas (8 g) was hydrogenated at 55 psi at room temp. for 24 h. The resultant mixture was filtered through a plug of Celite, and the filtrate concentrated under vacuum. The residue was subjected to column chromatography on silica gel eluting with a 1:1 mixture of 5% methanol in chloroform and chloroform saturated with ammonia gas. Collection and concentration of appropriate fractions provided the title triamine as clear, colorless, viscous oil. FAB MS m/e 310 (M+1)

Step B:

Preparation of 8-Benzyl-1-(3-methylphenyl)-1,3,8-triaza-spiro[4.5]decan-2-one

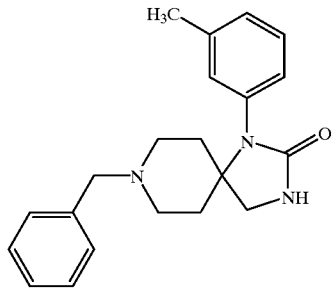

A mixture of 1-benzyl-4-(3-methylphenyl)-4-aminomethyl-piperidine (0.52 g, 1.67 mmol) and 1,1'-carbonyldiimidazole (0.41 g, 2.5 mmol) in dichloromethane (2 mL) was stirred at room temp. for 3 days. The resultant solution was concentrated and the residue subjected to column chromatography on silica gel eluting with a 1:1 mixture of chloroform and chloroform saturated with ammonia gas. Collection and concentration of appropriate fractions provide the title compound. FAB MS m/e 336 (M+1)

Step C:

Preparation of 4-{5-[2-Oxo-1-(3-methylphenyl)-1,3,8-triaza-spiro[4.5]dec-8-ylmethyl]imidazol-1-ylmethyl}benzonitrile

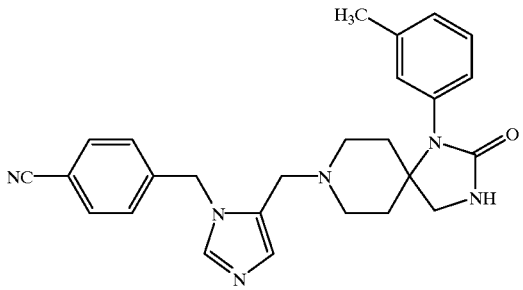

The title compound was prepared using the protocol described in Example 2, Steps D–E, substituting 8-benzyl-1-( 3-methylphenyl)-1,3,8-triaza-spiro[4.5]dec-2-en-4-one with 8-benzyl-1-(3-methylphenyl)-1,3,8-triaza-spiro[4.5]decan-2-one used in Step D.

Anal. Calcd for $C_{26}H_{28}N_6O \cdot 0.1\ Et_2O \cdot 0.2\ H_2O$: C, 70.21; H, 6.56; N, 18.61. Found: C, 70.23; H, 6.59; N, 18.65.

Example 6

Preparation of 4-{5-[2,2-Dioxo-1-(3-methylphenyl)-2-thia-1,3,8-triazaspiro[4.5]dec-8-ylmethyl]imidazol-1-ylmethyl}benzonitrile

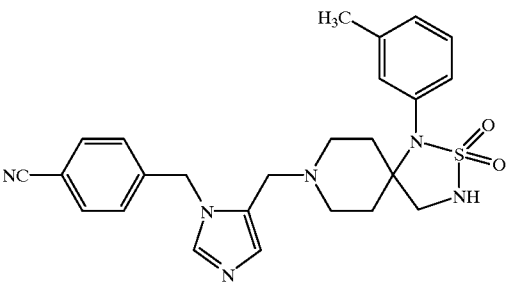

Step A:
Preparation of 8-Benzyl-2,2-dioxo-1-(3-methylphenyl)-2-thia-1,3,8-triazaspiro[4.5]decane

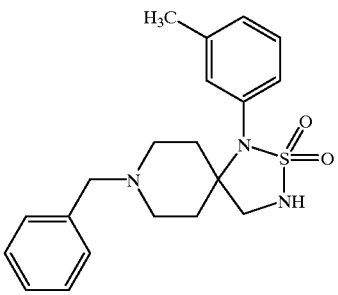

To a cold (−78° C.) solution of 1-benzyl-4-(3-methylphenyl)-4-aminomethylpiperidine (0.51 g, 1.66 mmol) in dichloromethane (10 mL), sulfuryl chloride (0.19 mL, 2.3 mmol) was added and the reacting mixture was stirred at room temp. for 3 days. The resultant solution was concentrated and the residue subjected to column chromatography on silica gel eluting with a 1:1 mixture of 3% methanol in chloroform and chloroform saturated with ammonia gas. Collection and concentration of appropriate fractions provide the title compound. FAB MS m/e 372 (M+1)

Step B:
Preparation of 4-{5-[2,2-Dioxo-1-(3-methylphenyl)-2-thia-1,3,8-triazaspiro[4.5]dec-8-ylmethyl]imidazol-1-ylmethyl}benzonitrile

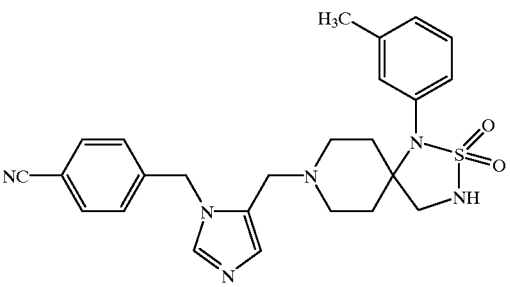

The title compound was prepared using the protocol described in Example 2, Steps D–E, substituting 8-benzyl-1-(3-methylphenyl)-1,3,8-triaza-spiro[4.5]dec-2-en-4-one with 8-benzyl-2,2-dioxo-1-(3-methylphenyl)-2-thia-1,3,8-triazaspiro[4.5]decane in Step D. The final product was subjected to high pressure liquid chromatography on C-18 stationary phase. Collection and lyophilization of appropriate fractions provided the title compound.

Anal. Calcd for $C_{25}H_{28}N_6O_2S \cdot 2.25$ TFA: C, 48.32; H, 4.16; N, 11.46. Found: C, 48.29; H, 4.13; N, 11.70.

Example 7

Preparation of 4-{5-[2,2-Dioxo-1-(4-chloro-3-methylphenyl)-2-thia-1,3,8-triazaspiro[4.5]dec-8-ylmethyl]imidazol-1-ylmethyl}benzonitrile

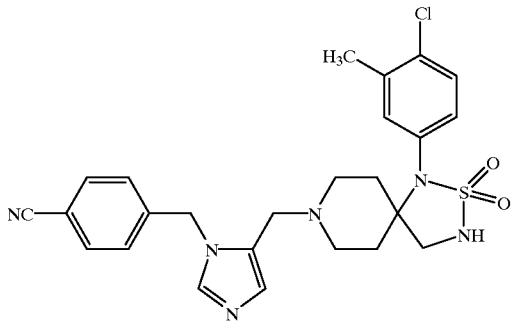

The title compound was isolated as a by-product during high pressure liquid chromatography purification of Example 6 in Step B.

Anal. Calcd for $C_{25}H_{27}N_6O_2ClS \cdot 0.15$ TFA $\cdot 0.55$ $H_2O$: C, 45.93; H, 3.98; N, 10.97. Found: C, 45.94; H, 4.08; N, 10.80.

Example 8

Preparation of 4-{5-[2-Oxo-1-(3-methylphenyl)-3-oxa-1,8-diazaspiro[4.5]dec-8-ylmethyl]imidazol-1-ylmethyl}benzonitrile

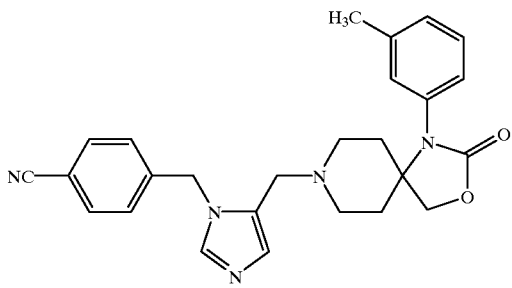

Step A:

Preparation of Ethyl 1-Benzyl-4-(3-methylphenylamino)-piperidine-4-carboxylate

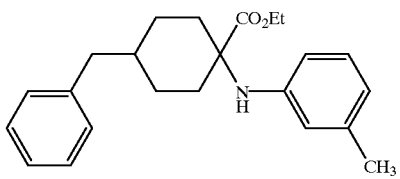

A solution of 1-benzyl-4-(3-methylphenylamino) isonipecotamide (4.5 g, 13.9 mmol), as described above in Example 2, Step B, and potassium hydroxide (3.g, 53.5 mmol) in ethylene glycol (35 mL) was heated under reflux. The resulting mixture was diluted with water and neutralized with acetic acid. The white solid precipitated was filtered, washed with chloroform to provide 1-benzyl-4-(3-methylphenylamino)piperidine-4-carboxylic acid.

A mixture of 1-benzyl-4-(3-methylphenylamino) piperidine-4-carboxylic acid (3.81 g, 11.7 mmol) and concentrated sulfuric acid (2 mL) in absolute ethanol (80 mL) was heated under reflux overnight. The resultant solution was concentrated under vacuum, and the residue was treated with chloroform saturated with ammonia gas. The mixture was filtered, and the filtrate concentrated. The residue was passed through a small plug of silica gel eluting with chloroform saturated with ammonia gas. Collection and concentration of the eluent under vacuum provided the title compound.

Step B:

Preparation of 1-Benzyl-4-hydroxymethyl-4-(3-methylphenylamino)piperidine

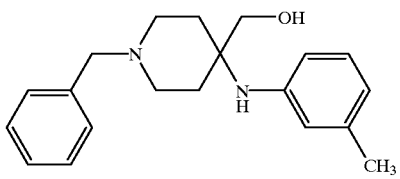

To a slurry of lithium aluminum hydride (330 mg, 8.7 mmol) in anhydrous diethyl ether (25 mL) at 0° C., a solution of ethyl 1-benzyl-4-(3-methylphenylamino) piperidine-4-carboxylate (2.8 g, 7.94 mmol) in diethyl ether (10 mL) was added dropwise with the temp. of the reacting mixture maintained below 10° C. The resulting mixture was stirred at 0° C. for 30 min, and quenched with successive addition of water (0.33 mL), 15% aqueous NaOH (0.33 mL), and water (1 mL). The resultant slurry was stirred at room temp. for 30 min., and was filtered through a small plug of Celite. The filtrate was washed brine, dried over anhydrous sodium sulfate, filtered, and concentrated under vacuum to provide the title alcohol as white solid.

Step C:

Preparation of 8-Benzyl-1-(3-methylphenyl)-3-oxa-1,8-diazaspiro[4.5]decan-2-one

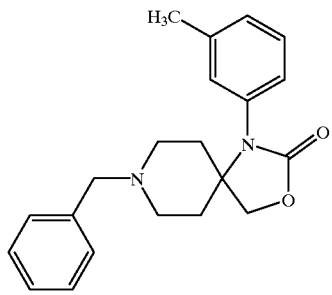

The title compound was prepared using the protocol described in Example 5, Step B substituting 1-benzyl-4-aminomethyl-4-(3-methylphenyl)piperidine with 1-benzyl-4-hydroxymethyl-4-(3-methylphenylamino)piperidine. The title compound was isolated by chromatography on silica gel. FAB MS m/e 337 (M+1).

Step D:

Preparation of 4-{5-[2-Oxo-1-(3-methylphenyl)-3-oxa-1,8-diazaspiro[4.5]dec-8-ylmethyl]imidazol-1-ylmethyl}-benzonitrile

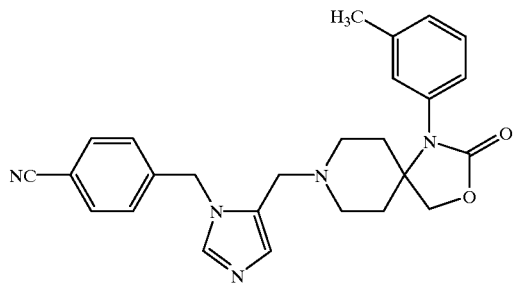

The title compound was prepared using the protocol described in Example 2, Steps D–E, substituting 8-benzyl-1-(3-methylphenyl)-1,3,8-triaza-spiro[4.5]dec-2-en-4-one with 8-benzyl-l1-(3-methylphenyl)-3-oxa-1,8-diazaspiro[4.5]decan-2-one used in Step D. FAB MS m/e 442 (M+1).

Example 9

Preparation of 4-[5-(1-Oxo-3,4-benzo-2,9-diazaspiro[5.5]undec-9-ylmethyl)imidazol-1-ylmethyl}benzonitrile

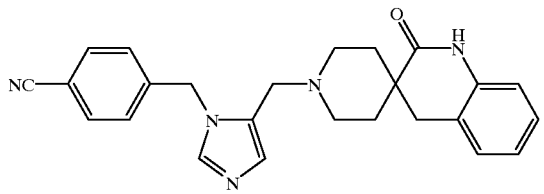

Step A:

Preparation of Ethyl N-tert-butoxycarbonylpiperidine-4-carboxylate

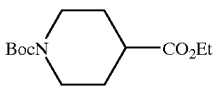

To a cold (0° C.) solution of ethyl isonipecotate (39.5g, 0.251 mol) and triethylamine (38.5 mL, 0.276 mol) in dichloromethane (350 mL), a solution of di-tert-butyl dicarbonate (55.9 g, 0.256 mol) in dichloromethane (50 mL) was added over a period of 30 min. The reacting mixture was stirred at room temp. overnight. The product mixture was washed with aqueous potassium hydrogen sulfate (3 times), and brine (to pH 7). The organic extract was dried over anhydrous sodium sulfate, filtered, and concentrated under vacuum to provide the title compound as clear, colorless, viscous oil.

Step B:

Preparation of Ethyl N-tert-butoxycarbonyl-4-(2-nitrobenzyl)piperidine-4-carboxylate

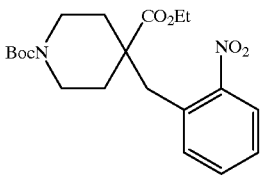

To a cold (–78° C.) solution of ethyl N-tert-butoxycarbonylpiperidine-4-carboxylate (7.5 g, 29 mmol) in anhydrous THF (75 mL), a solution of sodium bis(trimethylsilyl)amide (40 mL, 1M, 40 mmol) was added over a period of 30 min. The resultant mixture was stirred at –78° C. for 1 h., and a solution of 2-nitrobenzyl bromide (7.6 g, 35) in THF (10 mL) was added. The reacting mixture was allowed to warm up to room temp. and stirred overnight. The product mixture was concentrated, and the residue partition between water and ethyl acetate. The organic extract was washed with brine, dried over anhydrous magnesium sulfate, filtered, and concentrated under vacuum. The residue was subjected to column chromatography on silica gel eluting with 20% ethyl acetate in hexane. Collection and concentration of appropriate fractions provided the title compound.

Step C:

Preparation of 9-tert-Butoxycarbonyl-3,4-benzo-2,9-diazaspiro[5.5]undecan-1-one

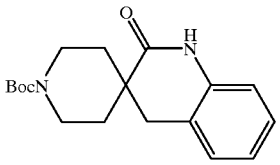

A mixture of ethyl N-tert-butoxycarbonyl-4-(2-nitrobenzyl)-piperidine-4-carboxylate (0.85 g, 2.17 mmol) and 5% palladium on charcoal (0.06 g) in ethanol (100 mL) was hydrogenated at room temp. at 50 psi overnight. The resultant mixture was filtered through a plug of Celite, and the filtrate concentrated under vacuum to provide the title compound.

Step D:

Preparation of 9-tert-Butoxycarbonyl-3,4-benzo-2,9-diazaspiro[5.5]undecan-1-one hydrochloride salt

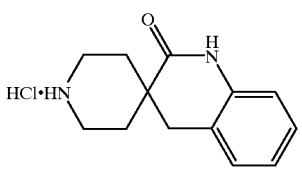

A solution of 9-tert-butoxycarbonyl-3,4-benzo-2,9-diazaspiro[5.5]undecan-1-one (0.25 g) in dichloromethane (40 mL) at 0° C. was saturated with hydrogen chloride gas. The resultant solution was sealed with a rubber septum and stirred at room temp. for 1 h. The product solution was concentrated under vacuum to provide the title compound.

Step E:

Preparation of 4-[5-(1-Oxo-3,4-benzo-2,9-diazaspiro[5.5]-undec-9-ylmethyl)imidazol-1-ylmethyl]benzonitrile

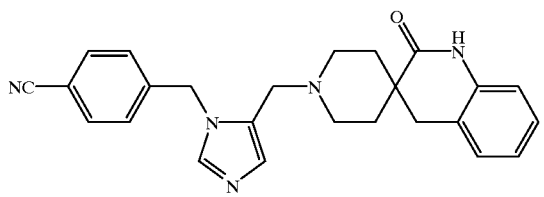

The title compound was prepared using the protocol described in Example 2, Step E substituting 1-(3-methylphenyl)-1,3,8-triaza-spiro[4.5]dec-2-en-4-one hydrochloride salt with 9-tert-butoxycarbonyl-3,4-benzo-2,9-diazaspiro[5.5]undecan-1-one hydrochloride salt.

Anal. Calcd for $C_{25}H_{25}N_5O$•0.1 $CHCl_3$•0.65 $H_2O$: C, 69.27; H, 6.12; N, 16.10. Found: C, 69.35; H, 6.15; N, 15.98.

Example 10

Preparation of 4-[5-(3,4-Benzo-8-azaspiro[4.5]-1-decen-8-ylmethyl)imidazol-1-ylmethyl]benzonitrile

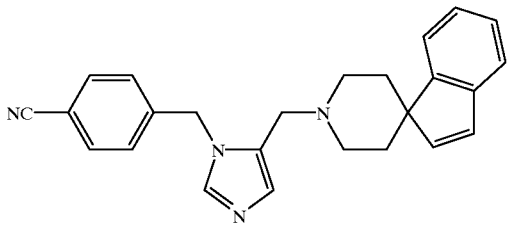

A mixture of spiro(1H-indene-1,4'-piperidine) (100 mg, 0.54 mmol (Journal of Medicinal Chemistry, vol. 35, p. 3919, (1992)), 1-(4-cyanobenzyl)imidazole-5-carboxyaldehyde (171 mg, 0.81 mmol), and a small amount of 4A sieves in 1,2-dichloroethane (3 mL) was stirred at room temp. for 15 min. The resultant mixture was treated with sodium triacetoxyborohydride (230 mg, 1.08 mmol) and stirred at room temp. overnight. The product mixture was diluted with dichloromethane and washed with sodium bicarbonate and brine. The organic extract was dried over anhydrous sodium sulfate, filtered, and concentrated under vacuum. The residue was subjected to column chromatography on silica gel eluting with a 95:5:0.5 v/v/v mixture of EtOAc:methanol:$NH_4OH$. Appropriate fractions were collected and concentrated under vacuum. The residual oil was dissolved in a 1:3 mixture of acetonitrile and water, and lyophilized to provide the title compound.

Anal. Calcd for $C_{25}H24N_4$: C, 78.92; H, 6.36; N, 14.73. Found: C, 77.81; H, 6.43; N, 14.52.

Example 11

Preparation of 4-[5-(4-Oxo-3-(3-trifluoromethoxybenzyl)-1-phenyl-1,3,8-triazaspir[4.5]dec-8-ylmethyl)imidazol-1-ylmethyl]benzonitrile dihydrochloride

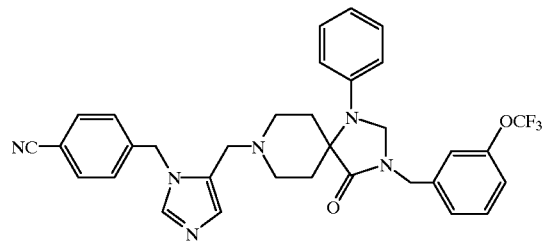

Step A:

Preparation of 1-phenyl-8-tert-butoxycabonyl-1,3,8-triazaspiro[4.5]-decan-4-one

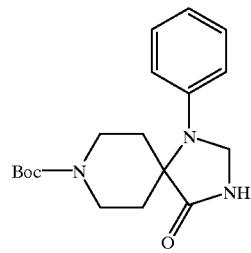

A solution of 1-phenyl-1,3,8-triazaspiro[4.5]decan-4-one (693 mg, 3 mmol) and di-tert-butyl dicarbonate (780 mg, 3.6 mmol) in anhydrous methylene chloride (10 mL) was stirred at room temp. for 24 hours. The resulting solution was concentrated under vacuum, and the residue was triturated with diethyl ether. The white solid which precipitated was collected by filtration to provide the title compound, mp: 214–216° C.

Step B:

Preparation of 1-phenyl-3-(3-trifluoromethoxybenzyl)-8-triazaspiro[4.5]-decan-4-one

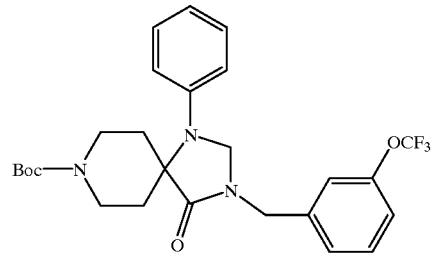

A solution of 1-phenyl-8-tert-butoxycarbonyl-1,3,8-triaza-spiro[4.5]decan-4-one, as described in Step A, (199 mg. 0.6 mmol) in anhydrous dimethyl-formamide (2 mL) was stirred at 50° C. with 60% sodium hydride in mineral oil (40 mg, 1 mmol) for 15 minutes under an inert (argon) atmosphere. 3-Trifluoromethoxybenzyl bromide (0.12 mL, 0.75 mmol) was added to the reaction. The reaction was heated for an additional 1.5 hours. The cooled reaction mixture was diluted with ethyl acetate and the organic layer washed successively with sat'd. aqueous sodium bicarbonate and water (3×). The resulting solution was dried (anhyd. sodium sulfate), filtered, and concentrated under vacuum, and the residue was subjected to column chromatography on silica gel eluting with a 20–30% ethyl acetate/hexane gradient. Appropriate fractions were combined and the solvent evaporated to give the title compound as viscous oil.

Step C:

Preparation of 1-phenyl-3-(3-trifluoromethoxybenzyl)-8-triazaspiro[4.5]-decan-4-one

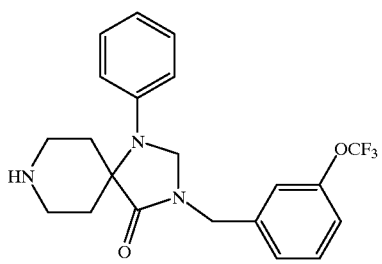

A solution of 1-phenyl-3-tert-butoxycarbonyl-8-tert-butoxycarbonyl-1,3,8-triaza-spiro[4.5]decan-4-one, as described above in Step B, (196 mg, 0.39 mmol) in anhydrous methylene chloride (6 mL) containing trifluoroacetic acid (0.5 mL) was stirred at ambient temp. for 20 hours. The solvent and excess TFA were removed under vacuum and the residue was redissolved in methylene chloride and washed with aqueous sat'd. sodium carbonate. The organic layer was dried (anhyd. sodium sulfate), filtered, and the solvent removed under vacuum to give the title compound as a viscous oil.

Step D:

Preparation of 4-{5-[4-Oxo-3-(3-trifluoromethoxybenzyl)-1-phenyl-1,3,8-triazaspiro[4.5]-dec-8-ylmethyl]imidazol-1-ylmethyl}benzonitrile Dihydrochloride

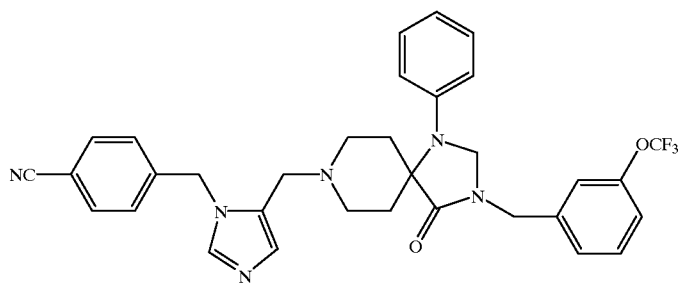

A solution of 1-phenyl-3-(3-trifluoromethoxybenzyl)-1,3,8-triazaspiro[4.5]decan-4-one, as described above in Step C, (159 mg, 0.39 mmol), 1-(4-cyanobenzyl)-5-chloromethylimidazole hydrochloride salt, as described in Example 1, Alternate Step A, (121 mg, 0.45 mmol), and triethylamine (0.21 mL, 1.5 mmol) in anhydrous acetonitrile (3 mL) was stirred at room temp. for 7 hours. The resulting mixture was diluted with ethyl acetate and the solution washed with sat'd aqueous sodium carbonate, dried (anhyd. sodium sulfate), filtered and concentrated under vacuum. The resulting residue was subjected to column chromatography on silica gel eluting with a 1–4% methanol(sat'd with ammonia)/ethyl acetate gradient. The appropriate fractions were collected and concentrated. The residue was dissolved in ethyl acetate and treated with two equivalents of 1M HCl/diethyl ether to afford the title compound as a dihydrochloride salt, mp: 240–241° C. Anal. Calcd for $C_{33}H_{31}F_3N_6O_2 \cdot 2$ HCl·0.25 H$_2$O: C,58.45; H, 4.98; N, 12.39. Found: C, 58.44; H, 4.99; N, 12.30. MS (ES$_+$) m/e 601.4 (m+1)

Example 12

Preparation of 4-[5-(4-Oxo-3-(2-trifluoromethoxybenzyl)-1-phenyl-1,3,8-triazaspiro[4.5]dec-8-ylmethyl)imidazol-1-ylmethyl]benzonitrile dihydrochloride

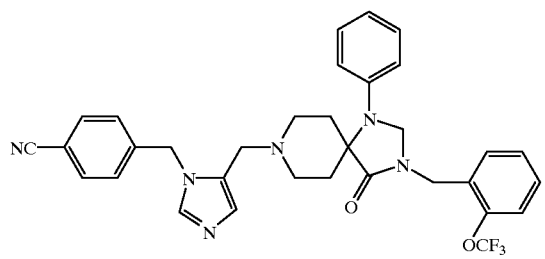

The title compound was prepared using the procedure described in Example 11, except substituting 2-trifluoromethoxybenzyl bromide for 3-trifluoromethoxybenzyl bromide in Step B to afford the dihydrochloride salt, mp:237–240° C.

Anal. Calcd for $C_{33}H_{31}F_3N_6O_2 \cdot 1.65$ HCl: C, 59.98; H, 4.98; N, 12.72. Found: C, 60.01; H, 4.90; N, 12.62. MS (ES$_+$) m/e 601.4 (m+1)

Example 13

Preparation of 4-[5-(2-Oxo-3-(3-trifluoromethoxybenzyl)-1-oxa-3,8-diaza-spiro[4.5] dec-8-ylmethyl)imidazol-1-ylmethyl]benzonitrile dihydrochloride

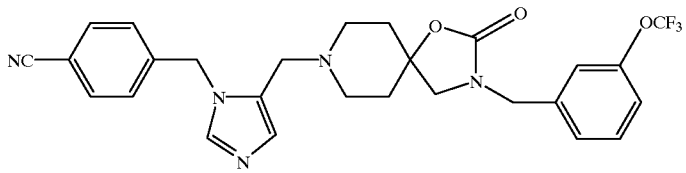

Step A:

Preparation of 1-Benzyl-4-hydroxy-4-aminomethyl piperidine

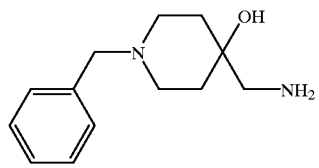

To neat 1-benzyl-4-piperidone (2.22 mL, 12 mmol) was added trimethylsilyl cyanide (1.95 mL, ~15 mmol) and zinc iodide (~5 mg). The solution was stirred for 6 hours or until reaction was completed as indicated by tlc. This oil was dissolved in diethyl ether (30 mL), filtered to remove some solid and added dropwise to a solution of diethyl ether (15 mL) containing 1M lithium aluminium hydride/diethyl ether (30 mL). After stirring at ambient temp. for 2 hours, the reaction was carefully quenched with aqueous sat'd sodium sulfate. This suspension was diluted with more diethyl ether, filtered to remove solids, and the solvent evaporated under partial vacuum to give the crude title compound as an oil.

Step B:

Preparation of 8-Benzyl-1-oxa-3,8-diaza-spiro[4.5]decan-2-one

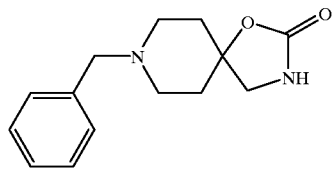

To a solution of crude 1-benzyl-4-hydroxy-4-aminomethyl piperidine, as described above in Step A, (~3.1 gm, 12 mmol) in acetonitrile (50 mL) containing triethyl amine (5.7 mL, 42 mmol) cooled in an ice bath was added in 1 mL portions 20% phosgene/toluene (9 mL) over a three hour period. The reaction mixture was stirred at ambient temp. for 15 hours and diluted with ethyl acetate. This solution was washed with water (2x) and the organic layer dried (anhyd. sodium sulfate), filtered, and the solvent removed under vacuum. The residue was triturated with diethyl ether and the title compound collected by filtration as a white solid, mp: 159–161° C.

Step C:

Preparation of 1-Oxa-3,8-diaza-spiro[4.5]decan-2-one acetate

A solution of 1-benzyl-1-oxa-3,8-diaza-spiro[4.5]decan-2-one, as described above in Step B, (496 mg, 2 mmol) in absolute ethanol (30 mL) containing acetic acid (2.4 mL) and 10% palladium/carbon (165 mg) was hydrogenated at atmospheric pressure for three hours. The catalyst was removed by filtration and the solvent removed under vacuum. The residue was chased with toluene (2x) to give a solid. This material was triturated with diethyl ether to give the title compound as a white solid as the acetate salt.

Step D:

Preparation of 8-tert-Butoxycarbonyl-1-oxa-3,8-diaza-spiro[4.5]deca-2-one

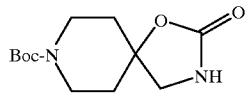

To a suspension of 1-oxa-3,8-diazaspiro[4.5]decan-2-one acetate, as described above in Step C, (410 mg, 1.9 mmol) in anhydrous methylene chloride (10 mL) was added di-tert-butyl dicarbonate (520 mg, 2.38 mmol) and triethyl amine (0.35 mL, 2.5 mmol) and the mixture stirred at room temp. for 3 hours to give a homogeneous solution. The resulting solution was diluted with more methylene chloride and washed with aqueous sat'd sodium bicarbonate. The organic layer was dried (anhyd. sodium sulfate) and the solvent removed under vacuum. The residue was triturated with diethyl ether and collected to give the title compound as a white solid, mp: 175–176° C.

Step E:

Preparation of 3-(3-trifluoromethoxybenzyl)-8-tert-butoxycarbonyl-1-oxa-3,8-diaza-spiro[4.5]deca-2-one

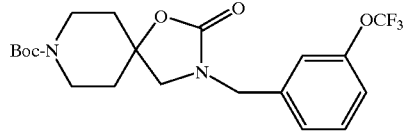

A solution of 8-tert-butoxycarbonyl-1-oxa-3,8-diaza-spiro[4.5]deca-2-one, as described above in Step D, (154 mg, 0.6 mmol) in anhydrous dimethyl-formamide (2 mL)

was stirred at 50° C. with 60% sodium hydride in mineral oil (34 mg, 0.85 mmol) for 15 minutes under an inert (argon) atmosphere. 3-Trifluoromethoxybenzyl bromide (0.11 mL, 0.7 mmol) was added to the reaction and heated for an additional 2 hours. The cooled reaction mixture was diluted with ethyl acetate and the organic layer washed successively with sat'd. aqueous sodium bicarbonate and water (3×). The resulting solution was dried (anhyd. sodium sulfate), filtered, and concentrated under vacuum, and the residue was subjected to column chromatography on silica gel eluting with a 10–50% ethyl acetate/hexane gradient. Appropriate fractions were combined and the solvent evaporated to give the title compound as a viscous oil.

Step F:
Preparation of 3-(3-trifluoromethoxybenzyl)-1-oxa-3,8-diaza-spiro[4.5]deca-2-one

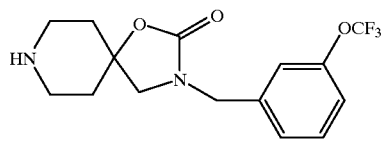

A solution of 3-tert-butoxycarbonyl-8-tert-butoxycarbonyl-1-oxa-3,8-diazaspiro[4.5]deca-2-one, as described above in Step E, (220 mg, 0.5]mmol) in anhydrous methylene chloride (5 mL) containing trifluoroacetic acid (0.5 mL) was stirred at ambient temp. for 4 hours. The solvent and excess TFA was removed under vacuum and the residue was redissolved in methylene chloride and washed with aqueous sat'd. sodium carbonate. The organic layer was dried (anhyd. sodium sulfate), filtered, and the solvent removed under vacuum to give the title compound as a viscous oil.

Step G:
Preparation of 4-[5-(2-Oxo-3-(3-trifluoromethoxybenzyl)-1-oxa-3,8-diaza-spiro[4.5]dec-8-ylmethyl)imidazol-1-ylmethyl]benzonitrile Dihydrochloride

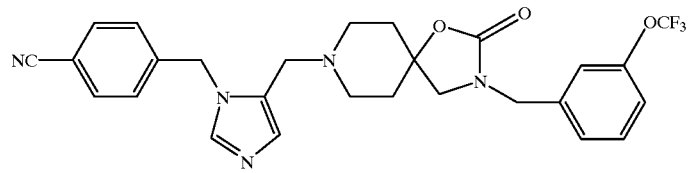

A solution of 3-(3-trifluoromethoxybenzyl)-1-oxa-3,8-diaza-spiro[4.5]deca-2-one, as described above in Step F, (164 mg, 0.50 mmol), 1-(4-cyanobenzyl)-5-chloromethylimidazole hydrochloride salt, as described in Example 1, Alternate Step A, (147 mg, 0.55 mmol), and triethylamine (0.21 mL, 1.5 mmol) in anhydrous acetonitrile (3 mL) was stirred at room temp. for 6 hours. The resulting mixture was diluted with ethyl acetate and the solution washed with sat'd aqueous sodium carbonate, dried (anhyd. sodium sulfate), filtered and concentrated under vacuum. The resulting residue was subjected to column chromatography on silica gel eluting with a 1–6% methanol (sat'd with ammonia)/ethyl acetate gradient. The appropriate fractions were collected and concentrated. The residue was dissolved in ethyl acetate and treated with two equivalents of 1M HCl/diethyl ether to afford the title compound as an amorphorous dihydrochloride salt.

Anal. Calcd for $C_{27}H_{26}F_3N_5O_3 \cdot 2$ HCl$\cdot$0.2 $H_2O$: C, 53.83; H, 4.54; N, 11.70. Found: C, 54.14; H, 4.72; N, 11.70. MS (ES$_+$) m/e 526.3 (m+1)

Example 14

Preparation of 4-[5-(2-Oxo-3-(2-trifluoromethoxybenzyl)-1-oxa-3,8-diaza-spiro[4.5]dec-8-ylmethyl)imidazol-1-ylmethyl]benzonitrile dihydrochloride

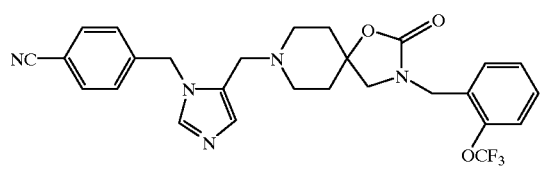

The title compound was prepared using the procedure described in Example 13, except substituting 2-trifluoromethoxybenzyl bromide for 3-trifluoromethoxybenzyl bromide in Step E to afford the dihydrochloride salt as an amorphorous solid.

Anal. Calcd for $C_{27}H_{26}F_3N_5O_3 \cdot 2$ HCl$\cdot$8.0 $H_2O$: C, 52.91; H, 4.87; N, 11.43. Found: C, 52.93; H, 4.96; N, 11.35.

Example 15

Preparation of 4-[5-(2-Oxo-3-n-butyl-1-oxa-3,8-diaza-spiro[4.5]dec-8-ylmethyl)imidazol-1-ylmethyl]benzonitrile dihydrochloride

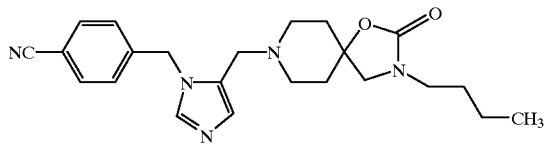

The title compound was prepared using the procedure described in Example 13, except substituting 1-bromobutane for 3-trifluoromethoxybenzyl bromide in Step E to afford the dihydrochloride salt as an amorphorous solid.

Anal. Calcd for $C_{23}H_{29}N_5O_2 \cdot 2$ HCl·0.5 $H_2O$: C, 56.44; H, 6.59; N, 14,31. Found: C, 56.38; H, 6.38; N, 14.51. MS(ES+) m/e 504.3 (m+1)

Example 16

Preparation of 4-[5-(2-Oxo-3-(2,2,2-trifluoroethyl)-1-oxa-3,8-diaza-spiro[4.5]dec-8-ylmethyl)imidazol-1-ylmethyl]benzonitrile dihydrochloride

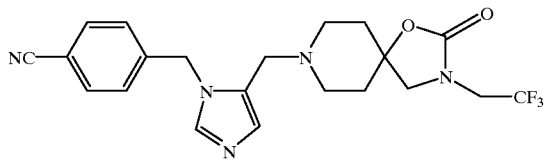

The title compound was prepared using the procedure described in Example 13, except substituting 2-iodo-1,1,1-trifluoroethane for 3-trifluoromethoxybenzyl bromide in Step E to afford the dihydrochloride salt as an amorphorous solid.

Anal. Calcd for $C_{21}H_{22}F_3N_5O_2 \cdot 2$ HCl: C, 46.16; H, 5.08; N, 13.83. Found: C, 49.81; H, 4.78; N, 13.83 MS(ES+) m/e 434.2 (m+1).

Example 17

Preparation of 4-[5-(spiro[3H-indole-3,4'-piperidin]-2(1H)-on-1'-ylmethyl)imidazol-1-ylmethyl]benzonitrile

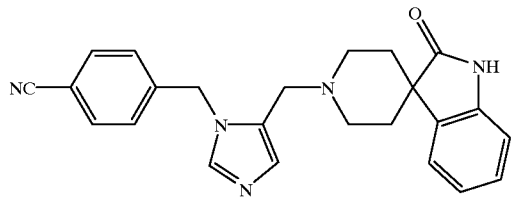

Step A:

Preparation of 1'-tert-butoxycarbonyl-spiro[3H-indole-3,4'-piperidin]-2(1H)-one

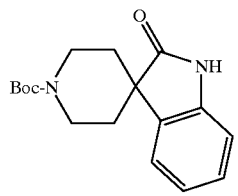

To a solution of oxindole (1.33 gm, 10 mmol) in anhydrous tetrahydrofuran (8 mL) was added dropwise, with ice bath cooling, 1 M lithium bis(trimethylsilyl)amide/tetrahydrofuran (30 mL, 30 mmol) under an inert atmosphere (argon). After 15 minutes, this greenish-brown solution was added dropwise to a solution of N-tert-butoxycarbonyl-bis(2-chloroethyl)amine (2.49 gm, 11 mmol) in anhydrous tetrahydrofuran (5 mL) which was also cooled in an ice bath under an inert atmosphere. This solution was stirred at ambient temp. over 20 hours. The reaction mixture was diluted with diethyl ether and acidified with 2 N HCl. The etheral layer was separated off and dried (anhyd. magnesium sulfate), filtered, and the solvent removed under vacuum. The residue was subjected to column chromatography on silica gel eluting with a 20–50% ethyl acetate/hexane gradient. The appropriate fractions were combined and the solvents concentrated to give a residue which was triturated with 2:1 hexane/diethyl ether to give the title compound as an off-white solid, mp: 138–140° C.

Step B:

Preparation of spiro[3H-indole-3,4'-piperidin]-2(1H)-one

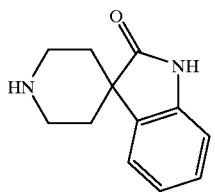

A solution of 1'-tert-butoxycarbonyl-spiro[3H-indole-3,4'-piperidin]-2(1H)-one, as described above in Step A, (551 mg, 1.70 mmol) in ethyl acetate saturated with HCl (5 mL) was stirred at ambient temp. for 3 hours as the product salt slowly crystallized out. This salt was collected by filtration and partitioned between methylene chloride and aqueous sat'd. sodium carbonate. The organic layer was separated off, dried (anhyd. sodium sulfate) filtered, and the solvent removed under vacuum. The residue was triturated with diethyl ether to give the title compound as a white solid, mp: 184–186° C.

Step C:

Preparation of 4-[5-(spiro[3H-indole-3,4'-piperidine]-2(1H)-on-1'-ylmethyl)imidazol-1-ylmethyl]benzonitrile

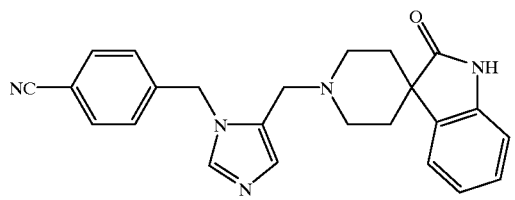

A solution of spiro[3H-indole-3,4'-piperidin]-2(1H)-one, as described above in Step B, (110 mg, 0.54 mmol), 1-(4-cyanobenzyl)-5-chloromethylimidazole hydrochloride salt, as described in Example 1, Alternate Step A, (134 mg, 0.50 mmol), and triethylamine (0.21 mL, 1.5 mmol) in anhydrous acetonitrile (1.5 mL) was stirred at room temp. for 15 hours. The resulting mixture was diluted with ethyl acetate and the solution washed with sat'd aqueous sodium carbonate, dried (anhyd. sodium sulfate), filtered and concentrated under vacuum. The resulting residue was triturated with ethyl acetate to give a white solid which was collected to afford the title compound as a crystalline freebase, mp: 245–247° C.

Anal. Calcd for $C_{26}H_{23}N_5O \cdot 0.5$ $H_2O$: C, 70.91; H, 5.95; N, 17.23. Found: C, 71.01; H, 6.00; N, 17.23.

Example 18

Preparation of 4-5-(1,3-Dioxo-2-(3-trifluoromethoxybenzyl)-2,8-diaza-spiro[4.5]dec-8-ylmethyl)imidazol-1-ylmethyl]benzonitrile dihydrochloride

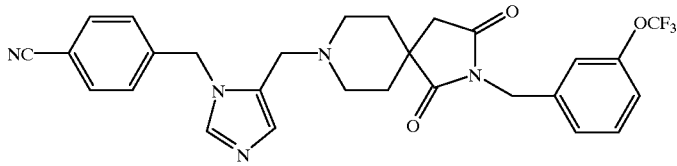

The title compound was prepared using the procedure described in Example 13, Steps C–G, except substituting 8-benzyl-2,8-diazaspiro[4.5]decan-1,3-dione [which can be prepared according to procedures described in Arch.Pharm., Vol. 294, 210–220(1961) and Swiss patent 383,968 (1965)] for 8-benzyl-1-oxa-3,8-diaza-spiro[4,5]decan-2-one in Step C to afford the dihydrochloride salt as an amorphorous solid.

Anal. Calcd for $C_{28}H_{26}F_3N_5O_3 \cdot 2$ HCl: C, 55.09; H, 4.62; N, 11.47. Found: C, 54.73; H, 4.32; N, 11.53. MS(ES$_+$) m/e 538.2 (m+1)

Example 19
In Vitro Inhibition of ras Farnesyl Transferase

Transferase Assays. Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 MM MgCl$_2$, 5 mM dithiothreitol, 10 μM ZnCl$_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor IC$_{50}$ determinations are as follows: FTase, 650 nM Ras-CVLS (SEQ.ID.NO.: 1), 100 nM farnesyl diphosphate.

The compounds of the instant invention described in the above Examples 1–18 were tested for inhibitory activity against human FPTase by the assay described above and were found to have IC$_{50}$ of ≦30 μM.

Example 20
Modified In vitro GGTase Inhibition Assay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ. ID.NO.: 2). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. IC$_{50}$ values are determined with Ras peptide near K$_M$ concentrations. Enzyme and substrate concentrations for inhibitor IC$_{50}$ determinations are as follows: 75 pM GGTase-I, 1.6 μM Ras peptide, 100 nM geranylgeranyl diphosphate.

The compounds of the instant invention described in the above Examples 1–18 are tested for inhibitory activity against human GGTase type I by the assay described above.

Example 21
Cell-based in vitro ras Farnesylation Assay

The cell line used in this assay is a v-ras line derived from either Rat1 or NIH$_3$T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 μCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 μL of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached

Example 22
Cell-based in vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 23
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI. The plasmid pGEM7zf(−)/SEAP was constructed as follows. The SEAP gene was PCRed, in two segments from a human placenta cDNA library (Clontech) using the following oligos.

Sense strand N-terminal SEAP: 5'GAGAGGGAAT-TCGGGCCCTTCCTGCAT GCTGCTGCTGCTGCT-GCTGGGC 3' (SEQ.ID.NO.:3) Antisense strand N-terminal SEAP: 5'GAGAGAGCTCGAGGTTAACCCGGGT GCGCGGCGTCGGTGGT 3' (SEQ.ID.NO.:4)

Sense strand C-terminal SEAP: 5'GAGAGAGTCTAGAGT-TAACCCGTGGTCC CCGCGTTGCTTCCT 3' (SEQ.ID.NO.:5)

Antisense strand C-terminal SEAP: 5'GAAGAGGAAGCT-TGGTACCGCCACTG GGCTGTAGGTGGTGGCT 3' (SEQ.ID.NO.:6)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 4) introduces an internal translation STOP codon within the SEAP gene along with the HpaI site. The C-terminal oligos (SEQ.ID.NO.: 5 and SEQ.ID.NO.: 6) were used to amplify a 412 bp C-terminal PCR product containing HpaI and HindIII restriction sites. The sense strand C-terminal oligo (SEQ.ID.NO.: 5) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electrophoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang et al, 1987) containing the CMV immediate early promoter was cut with EcoRI generating two fragments. The vector fragment was isolated by agarose electrophores is and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand: 5'GGCAGAGCTCGTTTAGTGAACCGTCAG 3' (SEQ.ID.NO.: 7)

Antisense strand: 5'GAGAGATCTCAAGGACGGTGACTGCAG 3' (SEQ.ID.NO.: 8)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP, contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Cloning of a Myristylated Viral-H-ras Expression Plasmid

A DNA fragment containing viral-H-ras can be PCRed from plasmid "H-1" (Ellis R. et al. J. Virol. 36, 408, 1980) or "HB-11 (deposited in the ATCC under Budapest Treaty on Aug. 27, 1997, and designated ATCC 209,218) using the following oligos.

Sense Strand: 5'TCTCCTCGAGGCCACCATGGGGAGTAGCAAGAGCAAGCCTAA GGACCCCAGCCAGCGCCGGATGACAGAATACAAGCTTGTGGTG G 3'. (SEQ.ID.NO.: 9)

Antisense: 5'CACATCTAGATCAGGACAGCACAGACTTGCAGC 3'. (SEQ.ID.NO.: 10)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site.

To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a viral-H-ras-CVLL expression plasmid

A viral-H-ras clone with a C-terminal sequence encoding the amino acids CVLL can be cloned from the plasmid "H-1" (Ellis R. et al., J. Virol. 36, 408, 1980) or "HB-11 (deposited in the ATCC under Budapest Treaty on Aug. 27, 1997, and designated ATCC 209,218) by PCR using the following oligos.

Sense strand: 5'TCTCCTCGAGGCCACCATGACAGAATACAAGCTTGTGGTGG-3' (SEQ.ID.NO.: 11)

Antisense Strand: 5'CACTCTAGACTGGTGTCAGAGCAGCACACACTTGCAGC-3' (SEQ.ID.NO.: 12)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense Strand: 5'-GAGAGAATTCGCCACCATGACGGAATATAAGCTGGTGG-3' (SEQ.ID.NO.: 13)

Antisense Strand: 5'-GAGAGTCGACGCGTCAGGAGAGCACACACTTG-C-3' (SEQ.ID.NO.: 14)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide: 5'-CCGCCGGCCTGGAGGAGTACAG-3' (SEQ.ID.NO.: 15)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense Strand: 5'-GAGAGAATTCGCCACCATGACTGAGTACAAACTGGTGG-3' (SEQ.ID.NO.: 16)

Antisense Strand: 5'-GAGAGTCGACTTGTTACATCACCACACATGGC-3' (SEQ.ID.NO.: 17)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI -Sal I cut mutagenes is vector pAlter-1 (Promega). Mutation of glycine-12 to a valine can be accomplished using the manufacturer's protocols and the following oligonucleotide: 5'-GTTGGAGCAGTTGGTGTTGGG-3' (SEQ.ID.NO.: 18)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.
Sense Strand:
5'-GAGAGGTACCGCCACCATGACTGAATATAAACT-TGTGG-3' (SEQ.ID.NO.: 19)
Antisense Strand:
5'-CTCTGTCGACGTATTTACATAATTACACACTTTGTC-3' (SEQ.ID.NO.: 20)

The primers will amplify a c-K-ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K-ras fragment can be ligated into a KpnI -Sal I cut mutagenes is vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 21)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay Human C33A cells (human epitheial carcenoma-ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 µl of $CaCl_2$-DNA solution is added dropwise while vortexing to 600 µl of 2× HBS buffer to give 1.2 ml of precipitate solution (see recipes below). This is allowed to sit at room temperature for 20 to 30 minutes. While the precipitate is forming, the media on the $C_{33}A$ cells is replaced with DMEM (minus phenol red; Gibco cat. #31053–028)+0.5% charcoal stripped calf serum+1× (Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1× (Pen/Strep, Glutamine and NEAA). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and test compound is for 36 hrs at 37° under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-CaPO$_4$ precipitate for 10 cm. plate of cells | |
| --- | --- |
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M CaCl$_2$ | 74 µl |
| dH$_2$O | 506 µl |
| 2X HBS Buffer | |
| 280 mM NaCl | |
| 10 mM KCl | |
| 1.5 mM Na$_2$HPO$_4$2H$_2$O | |
| 12 mM dextrose | |
| 50 mM HEPES | |
| Final pH = 7.05 | |
| Luminesence Buffer (26 ml) | |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |
| Assay Buffer | |
| Add 0.05M Na$_2$CO$_3$ to 0.05M NaHCO$_3$ to obtain pH 9.5. Make 1 mM in MgCl$_2$ | |

Example 24

The processing assays employed in this example and in Example 25 are modifications of that described by DeClue et al [Cancer Research 51, 712–717, 1991].

K4B-Ras Processing Inhibition Assay

PSN-1 (human pancreatic carcinoma) cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 µM), a compound that blocks Ras processing in cells by inhibiting a rate-limiting step in the isoprenoid biosynthetic pathway, serve as a positive control.

Test compounds are prepared as 1000×concentrated solutions in DMSO to yield a final solvent concentration of 0.1%. Following incubation at 37° C. for two hours 204 µCi/ml [$^{35}$S]Pro-Mix (Amersham, —cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 µg/ml AEBSF, 10 µg/ml aprotinin, 2 µg/ml leupeptin and 2 µg/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 µg of the pan Ras monoclonal antibody, Y13–259, added. The protein/antibody mixture is incubated on ice at 4° C. for 24 hours. The immune complex is collected on pansorbin (Calbiochem) coated with rabbit antiserum to rat IgG (Cappel) by tumbling at 40C for 45 minutes. The pellet is washed 3 times with 1 ml of lysis buffer lacking DTT and protease inhibitors and resuspended in 100µ elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 µg Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to HDJ-2 (Neomarkers Cat. #MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of HDJ (the slower-migrating species) is calculated by densitometry. Dose-response curves and IC50 values are generated using 4-parameter curve fits in SigmaPlot software.

Example 25

K4B-Ras Processing Inhibition Assay

PSN-1 (human pancreatic carcinoma) cells are used for analysis of protein processing. Subconfluent cells in 150 mm dishes are fed with 20 ml of media (RPMI supplemented with 15% fetal bovine serum) containing the desired concentration of prenyl-protein transferase inhibitor or solvent alone. Cells treated with lovastatin (5–10 µM), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%.

The cells are incubated at 37° C. for 24 hours, the media is then removed and the cells are washed twice with cold PBS. The cells are scraped into 2 ml of cold PBS, collected by centrifugation (10,000×g for 5 min at 4° C.) and frozen at −70° C. Cells are lysed by thawing and addition of lysis buffer (50 mM HEPES, pH 7.2, 50 mM NaCl, 1% CHAPS, 0.7 µg/ml aprotinin, 0.7 µg/ml leupeptin 300 µ/ml pefabloc, and 0.3 mM EDTA). The lysate is then centrifuged at 100,000×g for 60 min at 4° C. and the supernatant saved. The supernatant may be subjected to SDS-PAGE, HPLC analysis, and/or chemical cleavage techniques.

The lysate is applied to a HiTrap-SP (Pharmacia Biotech) column in buffer A (50 mM HEPES pH 7.2) and resolved by gradient in buffer A plus 1 M NaCl. Peak fractions containing Ki4B-Ras are pooled, diluted with an equal volume of water and immunoprecipitated with the pan Ras monoclonal antibody, Y13-259 linked to agarose. The protein/antibody mixture is incubated at 4° C. for 12 hours. The immune complex is washed 3 times with PBS, followed by 3 times with water. The Ras is eluted from the beads by either high pH conditions (pH>10) or by heating at 95° C. for 5 minutes, after which the beads are pelleted by brief centrifugation. The supernatant may be subjected to SDS-PAGE, HPLC analysis, and/or chemical cleavage techniques.

Example 26

Rap1 Processing Inhibition Assay

Protocol A:

Cells are labeled, incubated and lysed as described in Example 25.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 µg of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 µl elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 µg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bisacrylamide:acrylamide, 1:100), and the Rap1 visualized by fluorography.

Protocol B:

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1× Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in ½-log dilutions. The range of final concentrations to be assayed is generally 0.1–100 µM. Four concentrations per compound is typical. The compounds are diluted so that each concentration is 1000× of the final concentration (i.e., for a 10 µM data point, a 10 mM stock of the compound is needed).

2 µL of each 1000× compound stock is diluted into 1 ml media to produce a 2× stock of compound. A vehicle control solution (2 µL DMSO to 1 ml media), is utilized. 0.5 ml of the 2× stocks of compound are added to the cells.

After 24 hours, the media is aspirated from the assay plates. Each well is rinsed with 1 ml PBS, and the PBS is aspirated. 180 µL SDS-PAGE sample buffer (Novex) containing 5% 2-mercaptoethanol is added to each well. The plates are heated to 100° C. for 5 minutes using a heat block containing an adapter for assay plates. The plates are placed on ice. After 10 minutes, 20 µL of an RNAse/DNase mix is added per well. This mix is 1 mg/ml DNaseI (Worthington Enzymes), 0.25 mg/ml Rnase A (Worthington Enzymes), 0.5M Tris-HCl $pH_{8.0}$ and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 µl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30 V (constant voltage). Immediately after transferring, the membranes are blocked overnight in 20 ml Western blocking buffer (2% nonfat dry milk in Western wash buffer ($PBS_+0.1\%$ Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical $SC_{1482}$) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C

This protocol allows the determination of an $EC_{50}$ for inhibition of processing of Rap1a. The assay is run as described in Protocol B with the following modifications. 20 µl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121; Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant® software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 27

In vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle or compound treatment group. Animals are dosed subcutaneously starting on day 1 and daily for the duration of the experiment. Alternatively, the prenyl-protein transferase inhibitor may be administered by a continuous infusion pump. Compound or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound illustrated by the formula I:

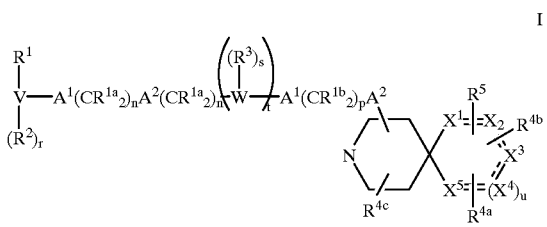

wherein:

$R^{1a}$ and $R^{1b}$ are independently selected from:
a) hydrogen, or
b) $C_1$–$C_6$ alkyl unsubstituted or substituted by unsubstituted or substituted aryl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—C($NR^8$)—, $R^8C(O)$—, $R^8OC(O)$—, $N_3$, —$N(R^8)_2$, or $R^9OC(O)$—$NR^8$—;

$R^1$ is selected from:
a) unsubstituted or substituted aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8{}_2N$—C($NR^8$)—, $R^8C(O)$—, $R^8OC(O)$—, $N_3$, —$N(R^8)_2$, or $R^9OC(O)NR^8$—, and
b) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—C(NH)—, $R^8C(O)$—, $R^8OC(O)$—, $N_3$, —$N(R^8)_2$, or $R^8OC(O)NH$—;

$R^2$ is independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, perfluoroalkyl, F, ClBr, $R^8O$—, $R^9S(O)_m$—, $R^8C(O)NR^8$—, CN, $NO_2$, $R^8{}_2N$—C($NR^8$)—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C$(O)NH—, CN, $H_2N$—C(NH)—, $R^8C(O)$—, $R^8OC(O)$—, $N_3$, —$N(R^8)_2$, or $R^8OC(O)NH$—;

$R^3$ is selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C$(O)$NR^8$—, CN, $NO_2$, $(R^8)_2N$—C—($NR^8$)—, $R^8C$(O)—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C$(O)$NR^8$—, CN, $(R^8)_2N$—C($NR^8$)—, $R^8C(O)$—, $R^8OC(O)$—, $N_3$, —$N(R^8)_2$, or $R^9OC(O)NR^8$—;

$R^{4a}$ and $R^{4b}$ independently are selected from:
H, =O, unsubstituted or substituted $C_{1-8}$ alkyl, or unsubstituted or substituted aryl;

$R^{4c}$ and $R^5$ independently are selected from:
H, =O, unsubstituted or substituted $C_{1-8}$ alkyl, unsubstituted or substituted $C_{2-8}$ alkenyl, unsubstituted or substituted aryl,

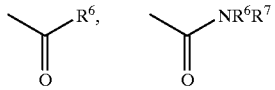

and —$S(O)_2R^6$, wherein the substituted group is substituted with one or more of:
1) aryl, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) —$NR^6R^7$

6)

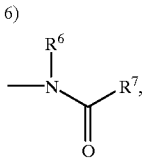

7)

―N(R⁶)―C(O)―NR⁷R⁷ᵃ,

8)

―O―C(O)―NR⁶R⁷ᵃ,

9)

―O―C(O)―OR⁶,

10)

―C(O)―NR⁶R⁷,

11)

―SO₂―NR⁶R⁷,

12)

―N(R⁶)―SO₂―R⁷,

13)

―C(O)―R⁶,

14)

―C(O)―OR⁶,

15) $C_{1-8}$ alkyl,
16) $C_{1-8}$ perfluoroalkyl, or
17) halo;

$R^6$, $R^7$ and $R^{7a}$ are independently selected from: H, $C_{1-4}$ alkyl, $C_{3-6}$ cycloalkyl, aryl, $C_{1-4}$ perfluoroalkyl, unsubstituted or substituted with one or two substituents selected from:
a) $C_{1-4}$ alkoxy,
b) substituted or unsubstituted aryl,
c) halogen,
d) HO, e) ―C(O)―R⁹, f) ―C(O)―OR⁸, g) ―S(O)ₘR⁹, or
h) N(R⁸)₂; or $R^8$ is independently selected from hydrogen, $C_1$–$C_6$ alkyl, benzyl, 2,2,2-trifluoroethyl and aryl;
$R^9$ is independently selected from $C_1$–$C_6$ alkyl and aryl;

$A^1$ and $A^2$ are bonds;
$X^1$ and $X^3$ are $N(H)_w$;
$X^2$ and $X^5$ are $C(H)_y$;
$X^4$ is selected from:
$C(H)_y$, $N(H)_w$, O, C=O, $S(O)_2$, and PO(OMe);
u is 0;
V is an aryl,
W is an imidazolyl;
m is 0, 1 or 2;
n is 0, 1, 2, 3 or 4;
p is 0 1, 2, 3 or 4;
r is independently 0 to 5;
s is 1 or 2;
t is 1;
w is 0 or 1; and
y is 1 or 2;
dashed lines represent optional double bonds
or the pharmaceutically acceptable salts or the optical isomers thereof.

2. The compound according to claim 1 the formula II:

$$V-A^1(CR^{1a}{}_2)_nA^2(CR^{1a}{}_2)_{\overline{n}} \cdots N=\overset{(R^3)_s}{\underset{N}{\bigcirc}} \cdots A^1(CR^{1b}{}_2)_pA^2 \cdots \overset{R^5}{\underset{R^{4a}}{\bigcirc}} \overset{X^1=X^2}{\underset{X^5=(X^4)_u}{\bigvee}} R^{4b}$$

II wherein
$R^{1a}$ and $R^{1b}$ are independently selected from:
  a) hydrogen, or
  b) $C_1$–$C_6$ alkyl unsubstituted or substituted by unsubstituted or substituted aryl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^1$ is selected from:
  a) unsubstituted or substituted aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8{}_2N$—$C(NR^8)$—, $R^8C(O)$—, $R^8OC(O)$—, $N_3$, —$N(R^8)_2$, or $R^9OC(O)NR^8$—, and
  b) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^2$ is independently selected from;
  a) hydrogen,
  b) unsubstituted or substituted aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8{}_2N$—$C(NR^8)$—, $R^8C(O)$—, $R^8OC(O)$—, $N_3$, —$N(R^8)_2$, or $R^9OC(O)NR^8$—, and
  c) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^3$ is selected from:
 a) hydrogen,
 b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—C—$(NR^8)$—, $R^8C(O)$—, $R^8OC(O)$—, $N_3$, —$N(R^8)_2$, or $R^9OC(O)NR^8$—, and
 c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^{4a}$ and $R^{4b}$ independently are selected from:
 H, =O, unsubstituted or substituted $C_{1-8}$ alkyl, unsubstituted or substituted aryl;

$R^5$ is selected from:
 H, =O, unsubstituted or substituted $C_{1-8}$ alkyl, unsubstituted or substituted $C_{2-8}$ alkenyl, unsubstituted or substituted aryl,

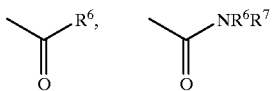

and $S(O)_2R^6$, wherein the substituted group is substituted with one or more of:
 1) aryl, unsubstituted or substituted with one or two groups selected from:
  a) $C_{1-4}$ alkyl,
  b) $(CH_2)_pOR^6$,
  c) $(CH_2)_pNR^6R^7$,
   d) halogen,
   e) $C_{1-4}$ perfluoroalkyl,
 2) $C_{3-6}$ cycloalkyl,
 3) $OR^6$,
 4) $SR^6$, $S(O)R^6$, $SO_2R^6$,
 5) —$NR^6R^7$ 6)
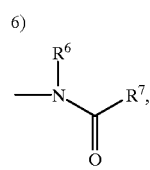

7)
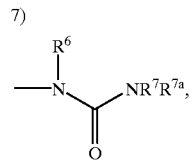

8)
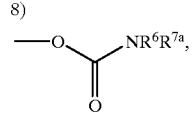

9)
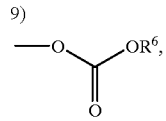

10)
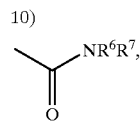

11)
—$SO_2$—$NR^6R^7$,

12)
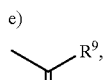

13)
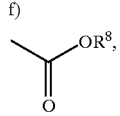

14)

15) $C_{1-8}$ alkyl,
16) $C_{1-8}$ perfluoroalkyl, or
17) halo;

$R^6$, $R^7$ and $R^{7a}$ are independently selected from: H, $C_{1-4}$ alkyl, $C_{3-6}$ cycloalkyl, aryl, $C_{1-4}$ perfluoroalkyl, unsubstituted or substituted with one or two substituents selected from:
 a) $C_{1-4}$ alkoxy,
 b) substituted or unsubstituted aryl,
 c) halogen,
 d) HO, e)

f)

g) —$S(O)_mR^9$, or
h) $N(R^8)_2$; or $R^8$ is independently selected from hydrogen, $C_1$–$C_6$ alkyl, benzyl, 2,2,2-trifluoroethyl and;

$R^9$ is independently selected from $C_1$–$C_6$ alkyl and aryl;
$A^1$ and $A^2$ are bonds;
$X^1$ and $X^3$ are $N(H)_w$;
$X^2$ and $X^5$ are $C(H)_y$;
u is 0;
$X^4$ is selected from:
 $C(H)_y$, $N(H)_w$, O, C=O, $S(O)_2$, and PO(OMe);
V is aryl;
m is 0, 1 or 2;
n is 0, 1, 2, 3 and 4;
p is 0, 1, 2, 3 and 4;
r is independently 0 to 5;
s is 1 or 2;
w is 0 or 1; and
y is 1 or 2;
dashed lines represent optional double bonds
or the pharmaceutically acceptable salts or the optical isomers thereof.

3. The compound according to claim 1 of the formula III:

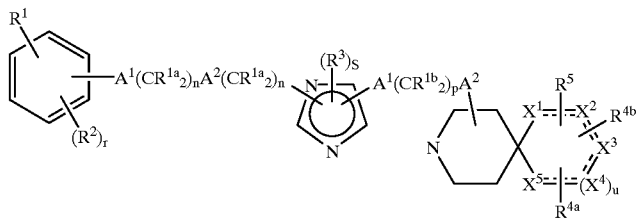

III wherein:

$R^{1a}$ and $R^{1b}$ are independently selected from:
a) hydrogen, or
b) $C_1$–$C_6$ alkyl unsubstituted or substituted by unsubstituted or substituted aryl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^1$ is selected from:
a) unsubstituted or substituted aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
b) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^2$ is independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^3$ is selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^{4a}$ and $R^{4b}$ independently are selected from:
H, =O, unsubstituted or substituted $C_{1-8}$ alkyl, unsubstituted or substituted aryl;

$R^5$ is selected from:
H, =O, unsubstituted or substituted $C_{1-8}$ alkyl, unsubstituted or substituted $C_{2-8}$ alkenyl, unsubstituted or substituted aryl,

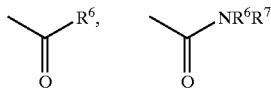

and —$S(O)_2R^6$, wherein the substituted group is substituted with one or more of:
1) aryl, unsubstituted or substituted with one or two groups selected from:
a) $C_{1-4}$ alkyl,
b) $(CH_2)_pOR^6$,
c) $(CH_2)_pNR^6R^7$,
d) halogen,
e) $C_{1-4}$ perfluoroalkyl,
2) $C_{3-6}$ cycloalkyl,
3) $OR^6$,
4) $SR^6$, $S(O)R^6$, $SO^2R^6$,
5) —$NR^6R^7$, 6)
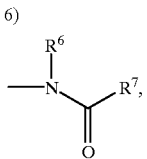

7)
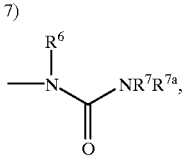

8)
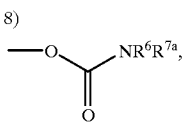

9)
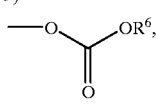

10)
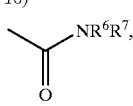

11)
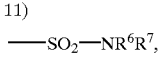

-continued

12)
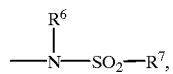

13)

14)
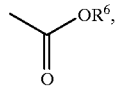

15) $C_{1-8}$ alkyl,
16) $C_{1-8}$ perfluoroalkyl, or
17) halo;

$R^6$, $R^7$ and $R^{7a}$ are independently selected from: H, $C_{1-4}$ alkyl, $C_{3-6}$ cycloalkyl, aryl, $C_{1-4}$ perfluoroalkyl, unsubstituted or substituted with one or two substituents selected from:

a) $C_{1-4}$ alkoxy,
b) substituted or unsubstituted aryl,
c) halogen,
d) HO, e)
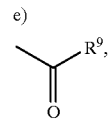

f)
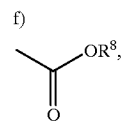

g) —$S(O)_m R^9$, or
h) $N(R^8)_2$; or $R^8$ is independently selected from hydrogen, $C_1-C_6$ alkyl, benzyl, 2,2,2-trifluoroethyl and aryl;

$R^9$ is independently selected from $C_1-C_6$ alkyl and aryl;

$A^1$ and $A^2$ are bonds;

$X^1$ and $X^3$ are $N(H)_w$;

$X^2$ and $X^5$ are $C(H)_y$;

u is 0;

$X^4$ is selected from:
$C(H)_y$, $N(H)_w$, O, C=O, $S(O)_2$, and PO(OMe);

m is 0, 1 or 2;

n is 0, 1, 2, 3 or 4;

p is 0, 1, 2, 3 or 4;

r is independently 0 to 5;

s is 1 or 2;

w is 0 or 1; and y is 1 or 2;

dashed lines represent optional double bonds or the pharmaceutically acceptable salts or the optical isomers thereof.

4. The compound according to claim 1 of the formula IV:

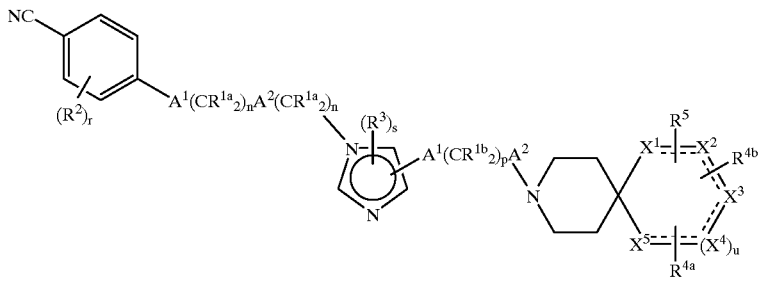

IV wherein
$R^{1a}$ and $R^{1b}$ are independently selected from:
a) hydrogen, or
b) $C_1-C_6$ alkyl unsubstituted or substituted by unsubstituted or substituted aryl, $C_3-C_{10}$ cycloalkyl, $C_2-C_6$ alkenyl, $C_2-C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^2$ is selected from:
a) unsubstituted or substituted aryl, $C_3-C_{10}$ cycloalkyl, $C_2-C_6$ alkenyl, $C_2-C_6$ alkynyl, perfluoroalkyl, F, Cl, Br, $R^8O$—, $R^9S(O)_m$—, $R^8C(O)NR^8$—, CN, $NO_2$, $R^8{}_2N$—$C(NR^8)$—, $R^8C(O)$—, $R^8OC(O)$—, $N_3$, —$N(R^8)_2$, or $R^9OC(O)NR^8$—, and
b) $C_1-C_6$ alkyl unsubstituted or substituted by aryl, $C_3-C_{10}$ cycloalkyl, $C_2-C_6$ alkenyl, $C_2-C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^3$ is selected from:
a) hydrogen,
b) $C_2-C_6$ alkenyl, $C_2-C_6$ alkynyl, $C_3-C_6$ cycloalkyl, perfluoroalkyl, F, Cl, Br, $R^8O$—, $R^9S(O)_m$—, $R^8C(O)NR^8$—, CN, $NO_2$, $(R^8)_2N$—C—$(NR^8)$—, $R^8C(O)$—, $R^8OC(O)$—, $N_3$, —$N(R^8)_2$, or $R^9OC(O)NR^8$—, and
c) $C_1-C_6$; alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^{4a}$ and $R^{4b}$ independently are selected from:
H, =O, unsubstituted or substituted $C_{1-8}$ alkyl, unsubstituted or substituted aryl;

$R^5$ is selected from:
H, =O, unsubstituted or substituted $C_{1-8}$ alkyl, unsubstituted or substituted $C_{2-8}$ alkenyl, unsubstituted or substituted aryl,

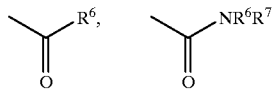

and $-S(O)_2R^6$, wherein the substituted group is substituted with one or more of:
1) aryl, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO^2R^6$,
5) $-NR^6R^7$ 6)
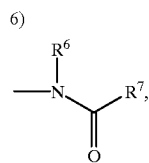

7)
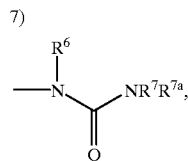

8)
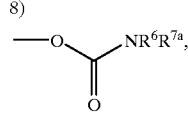

9)
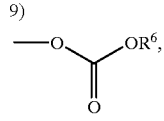

10)
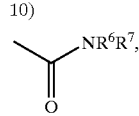

11)
$-SO_2-NR^6R^7$,

12)
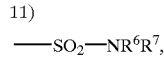

13)
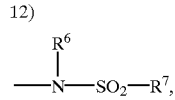

14)
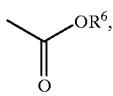

15) $C_{1-8}$ alkyl,
16) $C_{1-8}$ perfluoroalkyl, or
17) halo;

$R^6$, $R^7$ and $R^{7a}$ are independently selected from: H, $C_{1-4}$ alkyl, $C_{3-6}$ cycloalkyl, aryl, $C_{1-4}$ perfluoroalkyl, unsubstituted or substituted with one or two substituents selected from:
a) $C_{1-4}$ alkoxy,
b) substituted or unsubstituted aryl,
c) halogen,
d) HO, e)

f)
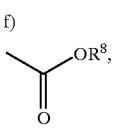

g) $-S(O)_mR^9$, or
h) $N(R^8)_2$; or $R^8$ is independently selected from hydrogen, $C_1$–$C_6$ alkyl, benzyl, 2,2,2-trifluoroethyl and aryl;
$R^9$ is independently selected from $C_1$–$C_6$ alkyl and aryl;
$A^1$ and $A^2$ are bonds;
$X^1$ and $X^3$ are NH;
$X^2$ and $X^5$ are $CH_2$;
u is 0;
$X^4$ is selected from:
  $C(H)_y$, $N(H)_w$, O, C=O, $S(O)_2$, and PO(OMe);
m is 0, 1 or 2;
n is 0, 1, 2, 3 or 4;
p is 0, 1, 2, 3 or 4;
r is 0, 1, 2, 3 or 4;
s is 1 or 2;
u is 0;
w is 0 or 1; and
y is 1 or 2;
dashed lines represent optional double bonds
or the pharmaceutically acceptable salts or the optical isomers thereof.

5. A compound selected from:
4-[5-(4-Oxo-1-phenyl-1,3,8-triazaspiro[4.5]dec-8-ylmethyl)imidazol-1-ylmethyl]benzonitrile;
4-{5-[4-Oxo-1-(3-methylphenyl)-1,3,8-triazaspiro[4.5]dec-8-ylmethyl]imidazol-1-ylmethyl}benzonitrile;
4-{5-[4-Oxo-1-(4-methylphenyl)-1,3,8-triazaspiro[4.5]dec-8-ylmethyl]imidazol-1-ylmethyl}benzonitrile;
4-{5-[2,4-Dioxo-1-(3-methylphenyl)-1,3,8-triaza-spiro[4.5]dec-8-ylmethyl]imidazol-1-ylmethyl}benzonitrile;
4-{5-[2-Oxo-1-(3-methylphenyl)-1,3,8-triaza-spiro[4.5]dec-8-ylmethyl]imidazol-1-ylmethyl}benzonitrile;

4-[5-(4-Oxo-3-(3-trifluoromethoxybenzyl)-1-phenyl-1,3,
8-triazaspiro[4.5]dec-8-ylmethyl)imidazol-1-ylmethyl]
benzonitrile;

4[5-(4-Oxo-3-(2-trifluoromethoxybenzyl)-1-phenyl-1,3,
8-triazaspiro[4.5]dec-8-ylmethyl)imidazol-1-ylmethyl]
benzonitrile;

or the pharmaceutically acceptable salts thereof.

6. The compound according to claim 5 which is:

4-{5-[4-Oxo-1-(3-methylphenyl)-1,3,8-triazaspiro[4.5]
dec-8-ylmethyl]imidazol-1-ylmethyl}benzonitrile

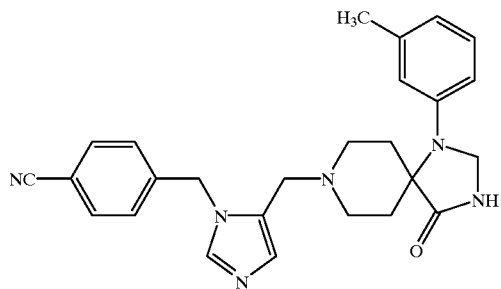

or its pharmaceutically acceptable salts.

7. The compound according to claim 5 which is:

4-{5-[2-Oxo-1-(3-methylphenyl)-1,3,8-triaza-spiro[4.5]
dec-8-ylmethyl]imidazol-1-benzonitrile

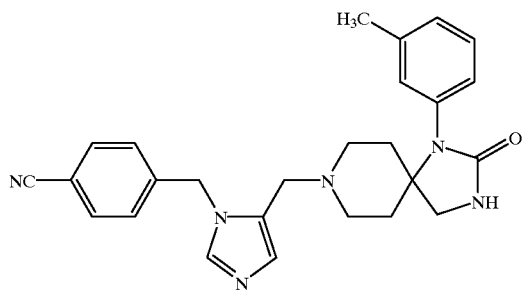

or its pharmaceutically acceptable salts.

8. The compound according to claim 5 which is:

4-{5-(4-Oxo-3-(3-trifluoromethoxybenzyl)-1-phenyl-1,3,
8-triazaspiro[4.5]dec-8-ylmethyl)imidazol-1-
ylmethyl}benzonitrile

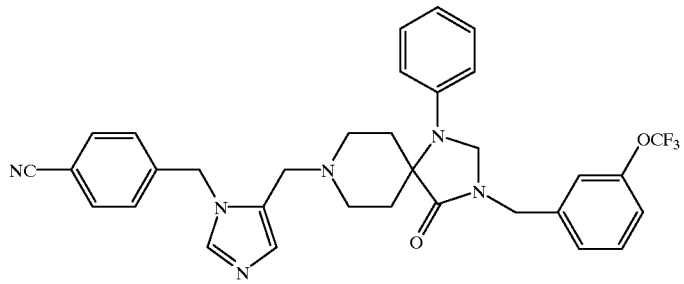

or its pharmaceutically acceptable salts.

9. The compound according to claim 5 which is:

4-[5-(4-Oxo-3-(2-trifluoromethoxybenzyl)-1-phenyl-1,3,
8-triazaspiro[4.5]dec-8-ylmethyl)imidazol-1-ylmethyl]
benzonitrile

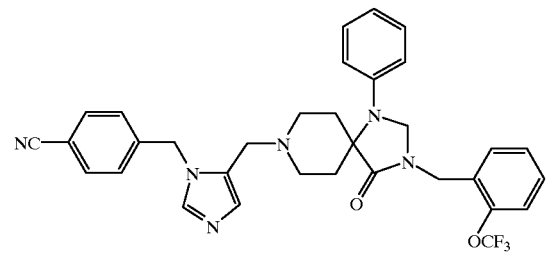

or its pharmaceutically acceptable salts.

10. A pharmaceutical composition comprising a pharmaceutical carrier, and dispersed therein, a therapeutically effective amount of a compound of claim 1.

11. A pharmaceutical composition comprising a pharmaceutical carrier, and dispersed therein, a therapeutically effective amount of a compound of claim 2.

12. A pharmaceutical composition comprising a pharmaceutical carrier, and dispersed therein, a therapeutically effective amount of a compound of claim 3.

13. A pharmaceutical composition comprising a pharmaceutical carrier, and dispersed therein, a therapeutically effective amount of a compound of claim 5.

14. A method for inhibiting farnesyl-protein transferase which comprises administering to a mammal in need thereof a therapeutically effective amount of a composition of claim 10.

15. A method for inhibiting farnesyl-protein transferase which comprises administering to a mammal in need thereof a therapeutically effective amount of a composition of claim 11.

16. A method for inhibiting farnesyl-protein transferase which comprises administering to a mammal in need thereof a therapeutically effective amount of a composition of claim 12.

17. A method for inhibiting farnesyl-protein transferase which comprises administering to a mammal in need thereof a therapeutically effective amount of a composition of claims 13.

18. A pharmaceutical composition made by combining the compound of claim 1 and a pharmaceutically acceptable carrier.

19. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 6,172,076 B1
DATED : January 9, 2001
INVENTOR(S) : Mark W. Embrey, John S. Wai, Debra S. Perlow and Jacob M. Hoffman It is certified that error appears in the above-identified patent and that said Letters Patent is hereby corrected as shown below:

Column 95, claim 1,
Line 8-13, the structure should be as follows:

-- 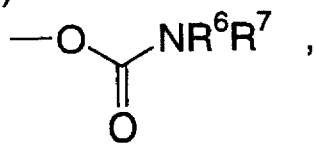 , --

Column 97, claim 2,
Lines 52-57, the structure should be as follows:

-- 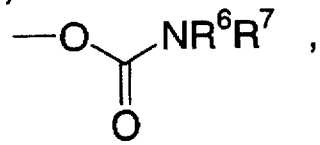 , --

Column 100, claim 3,
Lines 50-54, the structure should be as follows:

-- 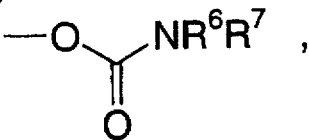 , --

Column 96, claim 2,
Line 24, should read -- 2. The compound according to claim 1 of the formula II: --.
The last line should read -- (O)-, $N_3$, -N($R^8$)$_2$, or $R^8$OC(O)NH-; --.

Column 97, claim 2,
Line 38, -- 5) -N$R^6R^7$, --.

UNITED STATES PATENT AND TRADEMARK OFFICE
CERTIFICATE OF CORRECTION

PATENT NO.   : 6,172,076 B1
DATED        : January 9, 2001
INVENTOR(S)  : Mark W. Embrey, John S. Wai, Debra S. Perlow and Jacob M. Hoffman It is certified that error appears in the above-identified patent and that said Letters Patent is hereby corrected as shown below:

Column 98, claim 2,
Line 46, should read as follows -- benzyl, 2,2,2-trifluorethyl and aryl; --.

Column 102, claim 4,
Line 61, should read as follows -- (O)NR$^8$-, CN, NO$_2$, (R$^8$)$_2$N-C-(NR$^8$)-, R$^8$C -- .

Column 103, claim 4,
Lines 26-27, should read as follows -- 4) SR$^6$, S(O)R$^6$, SO$_2$R$^6$,
                                        5) -NR$^6$R$^7$, -- .

Column 105, claim 7,
Line 28, should read as follows -- dec-8- ylmethyl]imidazol-1-ylmethyl}benzonitrile --.

Signed and Sealed this

Eighth Day of January, 2002

Attest:

JAMES E. ROGAN
Director of the United States Patent and Trademark Office

Attesting Officer